US012565632B2

(12) United States Patent
Foody et al.

(10) Patent No.: US 12,565,632 B2
(45) Date of Patent: *Mar. 3, 2026

(54) PROCESS AND SYSTEM FOR PRODUCING BIOFUELS WITH REDUCED CARBON INTENSITY

(71) Applicant: Iogen Corporation, Ottawa (CA)

(72) Inventors: Patrick J. Foody, Ottawa (CA); John Dechman, Ottawa (CA)

(73) Assignee: Iogen Corporation, Ottawa (CA)

( * ) Notice: Subject to any disclaimer, the term of this patent is extended or adjusted under 35 U.S.C. 154(b) by 865 days.

This patent is subject to a terminal disclaimer.

(21) Appl. No.: 17/758,202

(22) PCT Filed: Dec. 21, 2020

(86) PCT No.: PCT/CA2020/051778
§ 371 (c)(1),
(2) Date: Jun. 29, 2022

(87) PCT Pub. No.: WO2021/142528
PCT Pub. Date: Jul. 22, 2021

(65) Prior Publication Data
US 2023/0053930 A1     Feb. 23, 2023

Related U.S. Application Data

(60) Provisional application No. 62/960,825, filed on Jan. 14, 2020.

(51) Int. Cl.
*C12M 1/00*     (2006.01)
*C02F 11/04*    (2006.01)
(Continued)

(52) U.S. Cl.
CPC ............ *C12M 21/12* (2013.01); *C02F 11/04* (2013.01); *C12M 47/18* (2013.01); *C12P 5/023* (2013.01);
(Continued)

(58) Field of Classification Search
CPC ...... C12M 21/12; C12M 43/04; C12M 47/18; C02F 11/04; C12P 5/023; Y02E 50/10
See application file for complete search history.

(56) References Cited

U.S. PATENT DOCUMENTS

| | | | |
|---|---|---|---|
| 4,380,242 A | 4/1983 | Bresie et al. | |
| 4,677,827 A * | 7/1987 | Shenoy ..................... | F02C 1/02 60/648 |

(Continued)

FOREIGN PATENT DOCUMENTS

| | | |
|---|---|---|
| CA | 2842759 | 2/2013 |
| CA | 2820733 | 7/2017 |

(Continued)

OTHER PUBLICATIONS

International Preliminary Report on Patentability mailed Jul. 28, 2022 for PCT Application No. PCT/CA2020/051778.
(Continued)

*Primary Examiner* — Ellen M McAvoy
*Assistant Examiner* — Ming Cheung Po
(74) *Attorney, Agent, or Firm* — Knobbe, Martens, Olson & Bear, LLP

(57) ABSTRACT

A process and/or system for producing one or more biofuels, wherein biogas (e.g., partially purified biogas produced by removing water, hydrogen sulfide and/or carbon dioxide from raw biogas) is transported by vehicle in one or mobile vessels. De-pressurization of the mobile vessels provides a change in pressure that can be used to provide work, cooling, and/or increased pressure for the production process. Combustion of the biogas produces heat and/or power used to reduce a carbon intensity of the biofuel or biofuel intermediate.

20 Claims, 10 Drawing Sheets

(51) Int. Cl.

| | |
|---|---|
| *C12P 5/02* | (2006.01) |
| *C12P 7/10* | (2006.01) |
| *C12P 7/649* | (2022.01) |
| *C12P 19/02* | (2006.01) |
| *C12P 19/14* | (2006.01) |

(52) U.S. Cl.

CPC ................. *C12P 7/10* (2013.01); *C12P 7/649*
(2013.01); *C12P 19/02* (2013.01); *C12P 19/14*
(2013.01)

(56) References Cited

U.S. PATENT DOCUMENTS

| | | | |
|---|---|---|---|
| 5,570,729 | A | 11/1996 | Mutter |
| 5,603,360 | A | 2/1997 | Teel |
| 6,112,528 | A | 9/2000 | Rigby |
| 6,932,121 | B1 | 8/2005 | Shivers, III |
| 7,381,550 | B2 | 6/2008 | Hallberg et al. |
| 7,604,743 | B2 | 10/2009 | Hirl |
| 7,691,182 | B1 | 4/2010 | Muradov et al. |
| 7,731,779 | B2 | 6/2010 | Palumbo |
| 8,007,567 | B2 | 8/2011 | Roe et al. |
| 8,367,378 | B2 * | 2/2013 | Balan ....................... C12P 7/10 |
| | | | 435/165 |
| 8,367,478 | B2 | 2/2013 | Bartley et al. |
| 8,373,305 | B2 | 2/2013 | Adam et al. |
| 8,404,025 | B2 | 3/2013 | Frisbie et al. |
| 8,549,877 | B2 | 10/2013 | Santos |
| 8,658,026 | B2 | 2/2014 | Foody et al. |
| 8,753,854 | B2 | 6/2014 | Foody |
| 8,833,088 | B2 | 9/2014 | Bayliff et al. |
| 8,945,373 | B2 | 2/2015 | Foody |
| 8,999,036 | B2 | 4/2015 | Pierce |
| 9,040,271 | B2 | 5/2015 | Foody |
| 9,108,894 | B1 | 8/2015 | Foody et al. |
| 9,145,300 | B1 | 9/2015 | Foody |
| 9,222,048 | B1 | 12/2015 | Foody |
| 9,234,627 | B2 | 1/2016 | Cajiga et al. |
| 9,243,190 | B2 | 1/2016 | Patience et al. |
| 9,506,605 | B2 | 11/2016 | Paget et al. |
| 9,514,464 | B2 | 12/2016 | Foody |
| 9,535,045 | B2 | 1/2017 | Gerhold |
| 9,605,286 | B2 | 3/2017 | Foody |
| 9,625,097 | B2 | 4/2017 | Bayliff et al. |
| 9,625,099 | B2 | 4/2017 | Ding |
| 9,644,792 | B2 | 5/2017 | Moszkowski et al. |
| 9,863,581 | B2 | 1/2018 | Santos et al. |
| 9,969,949 | B1 | 5/2018 | Foody et al. |
| 10,093,540 | B2 | 10/2018 | Foody |
| 10,132,447 | B2 | 11/2018 | Whiteman et al. |
| 10,183,267 | B2 | 1/2019 | Day et al. |
| 10,202,622 | B2 | 2/2019 | Foody et al. |
| 10,421,663 | B2 | 9/2019 | Foody |
| 10,487,282 | B2 | 11/2019 | Foody et al. |
| 10,619,173 | B2 | 4/2020 | Foody et al. |
| 10,640,793 | B2 | 5/2020 | Foody et al. |
| 10,723,621 | B2 | 7/2020 | Foody |
| 10,760,024 | B2 | 9/2020 | Foody et al. |
| 10,894,968 | B2 | 1/2021 | Foody et al. |
| 10,968,151 | B1 | 4/2021 | Whitmore |
| 10,981,784 | B2 | 4/2021 | Foody |
| 11,220,470 | B2 | 1/2022 | Whitmore |
| 11,299,686 | B2 * | 4/2022 | Foody ..................... F23D 14/28 |
| 11,434,509 | B2 | 9/2022 | Foody et al. |
| 11,708,313 | B2 | 7/2023 | Whitmore |
| 11,746,301 | B2 * | 9/2023 | Foody ....................... C01B 3/38 |
| | | | 518/702 |
| 11,760,630 | B2 | 9/2023 | Foody |
| 11,827,916 | B2 | 11/2023 | Foody et al. |
| 11,946,001 | B2 | 4/2024 | Foody |
| 11,946,006 | B2 | 4/2024 | Foody et al. |
| 12,241,036 | B2 * | 3/2025 | Foody ..................... C12P 5/023 |
| 12,312,547 | B2 | 5/2025 | Foody et al. |
| 12,338,406 | B2 | 6/2025 | Foody et al. |
| 12,359,134 | B2 | 7/2025 | Foody |

| | | | |
|---|---|---|---|
| 2003/0225169 | A1 | 12/2003 | Yetman |
| 2006/0213370 | A1 | 9/2006 | Leonard et al. |
| 2007/0157804 | A1 | 7/2007 | McManus et al. |
| 2008/0134754 | A1 | 6/2008 | Funk |
| 2008/0209916 | A1 | 9/2008 | White |
| 2010/0000153 | A1 | 1/2010 | Kurkjian et al. |
| 2010/0108567 | A1 | 5/2010 | Medoff |
| 2011/0084020 | A1 | 4/2011 | Ott |
| 2012/0090325 | A1 | 4/2012 | Lewis |
| 2012/0308989 | A1 | 12/2012 | Barclay et al. |
| 2013/0161235 | A1 | 6/2013 | Foody |
| 2013/0183705 | A1 | 7/2013 | Barclay et al. |
| 2013/0224808 | A1 | 8/2013 | Bell et al. |
| 2014/0227751 | A1 | 8/2014 | Datta et al. |
| 2014/0349360 | A1 | 11/2014 | Zhang et al. |
| 2014/0370559 | A1 | 12/2014 | Oakley et al. |
| 2015/0101671 | A1 | 4/2015 | Paget et al. |
| 2015/0211684 | A1 * | 7/2015 | Santos .................. F17C 11/007 |
| | | | 137/1 |
| 2015/0345708 | A1 | 12/2015 | Sloan et al. |
| 2016/0178128 | A1 | 6/2016 | Le Bruchec et al. |
| 2016/0245459 | A1 | 8/2016 | Grimmer et al. |
| 2016/0247183 | A1 | 8/2016 | Foody |
| 2016/0281927 | A1 | 9/2016 | Bjorn et al. |
| 2016/0290563 | A1 | 10/2016 | Diggins |
| 2017/0074583 | A1 | 3/2017 | Tremblay |
| 2017/0130901 | A1 | 5/2017 | Sloan et al. |
| 2017/0241592 | A1 | 8/2017 | Whiteman et al. |
| 2017/0304769 | A1 | 10/2017 | Bigeard et al. |
| 2018/0079672 | A1 | 3/2018 | Meyer |
| 2018/0094772 | A1 | 4/2018 | Santos et al. |
| 2018/0112142 | A1 | 4/2018 | Foody et al. |
| 2018/0138528 | A1 | 5/2018 | Komiya |
| 2018/0155649 | A1 | 6/2018 | Gerhold |
| 2018/0251372 | A1 | 9/2018 | Foody |
| 2019/0001263 | A1 | 1/2019 | Prince |
| 2019/0030482 | A1 | 1/2019 | Ding |
| 2019/0144890 | A1 | 5/2019 | Subbian et al. |
| 2019/0144895 | A1 | 5/2019 | Foody et al. |
| 2019/0185884 | A1 | 6/2019 | Foody |
| 2019/0224617 | A1 | 7/2019 | Mitariten |
| 2019/0262770 | A1 | 8/2019 | Thygesen |
| 2020/0140901 | A1 | 5/2020 | Foody et al. |
| 2020/0148964 | A1 | 5/2020 | Foody et al. |
| 2020/0318896 | A1 | 10/2020 | Prince et al. |
| 2021/0055046 | A1 | 2/2021 | Prince |
| 2021/0060486 | A1 | 3/2021 | Prince |
| 2021/0094894 | A1 | 4/2021 | Whitmore |
| 2021/0155864 | A1 | 5/2021 | Foody et al. |
| 2021/0172677 | A1 | 6/2021 | Terrien et al. |
| 2021/0275961 | A1 | 9/2021 | Foody et al. |
| 2021/0317377 | A1 | 10/2021 | Foody et al. |
| 2021/0324282 | A1 | 10/2021 | Foody et al. |
| 2022/0177792 | A1 | 6/2022 | Foody et al. |
| 2022/0267688 | A1 | 8/2022 | Foody et al. |
| 2023/0295523 | A1 | 9/2023 | Foody |
| 2024/0025739 | A1 | 1/2024 | Foody |
| 2024/0123399 | A1 | 4/2024 | Buckenham |
| 2024/0209272 | A1 | 6/2024 | Foody et al. |
| 2025/0084334 | A1 | 3/2025 | Foody et al. |
| 2025/0250499 | A1 | 8/2025 | Foody et al. |

FOREIGN PATENT DOCUMENTS

| | | |
|---|---|---|
| DE | 10 2013 011 289 | 1/2015 |
| EP | 0 207 277 | 1/1990 |
| EP | 3 085 766 | 10/2016 |
| EP | 4 043 089 | 8/2022 |
| WO | WO 2010/006910 | 1/2010 |
| WO | WO 2011/101137 | 8/2011 |
| WO | WO 2013/021140 | 2/2013 |
| WO | WO 2017/195103 | 11/2017 |
| WO | WO 2018/144328 | 8/2018 |
| WO | WO 2019/185315 | 10/2019 |
| WO | WO 2020/010430 | 1/2020 |
| WO | WO 2020/010431 | 1/2020 |
| WO | WO 2020/041857 | 3/2020 |

(56)                    References Cited

FOREIGN PATENT DOCUMENTS

| WO | WO 2021/003564 | 1/2021 |
| WO | WO 2021/142528 | 7/2021 |
| WO | WO 2022/147610 | 7/2022 |

OTHER PUBLICATIONS

European Search Report in EP Application No. 20914142.3 dated Jun. 15, 2023.

Hovland, Jon, "Kompresjon av ra biogass", Tel-Tek. Obtained Oct. 27, 2023.

Office Action issued in Canadian application No. 3,163,078 on Dec. 7, 2023.

"Good Practices and Innovations in the Biogas Industry", European Biogas Association, Jan. 2018 (downloaded Aug. 28, 2019), in 100 pages. URL: http://european-biogas.eu/wp-content/uploads/2018/02/Success-Stories-EBA-2018.pdf.

"IPCC Fourth Assessment Report: Climate Change 2007, 5.3.1.3 Alternative fuels—AR4 WGIII Chapter 5: Transport and its infrastructure", IPCC, accessed Oct. 14, 2020, in 5 pages. URL: https://archive.ipcc.ch/publications_and_data/ar4/wg3/en/ch5s5-3-1-3.html.

Beilstein et al., "Ethanol producers need to reduce their CI score—and quickly", Ethanol Producer Magazine, Oct. 31, 2019, in 5 pages. URL: http://ethanolproducer.com/articles/16668/ethanol-producers-need-to-reduce-their-ci-scoreundefinedand-quickly.

Biswas et al., "Biofuels and Their Production Through Different Catalytic Routes", Chemical and Biochemical Engineering Quarterly, Apr. 2017, vol. 31, pp. 47-62.

Hakawati et al., "What is the most energy efficient route for biogas utilization: Heat, electricity or transport?", Applied Energy, Nov. 2017, vol. 206, pp. 1076-1087.

Heijstra et al., "Gas Fermentation: Cellular Engineering Possibilities and Scale Up", Microbial Cell Factories, Apr. 2017, vol. 16, in 11 pages.

Hengeveld et al., "When does decentralized production of biogas and centralized upgrading and injection into the natural gas grid make sense?", Biomass and Bioenergy, Jun. 2014, vol. 67, pp. 363-371.

Hengeveld et al., "Biogas infrastructures from farm to regional scale, prospects of biogas transport grids", Biomass and Bioenergy, Mar. 2016, vol. 86, pp. 43-52.

Hjort, A. et al., "Transport Alternatives for Biogas", BioMil AB, Nov. 2012, in 35 pages.

Hovland et al., "Compression and Transport of Raw Biogas", Sintef Tel-tek, 2019, in 32 pages.

Hovland, J. et al., "Compression of raw biogas—A feasibility study", Tel-Tek, Apr. 2017, Report No. 2217020-1, in 12 pages.

Kapoor, R. et al., "Seventh Framework Programme Theme Energy", 7 Cooperation, downloaded on Aug. 27, 2019, in 59 pages. URL: http://www.valorgas.soton.ac.uk/Deliverables/120825_VALORGAS_241334_D5-2_rev[0].pdf.

Krich K. et al., "Chapter 4—Storage and Transportation of Biogas Biomethane", Biomethane from Dairy Waste: A Sourcebook for the Production and Use of Renewable Natural Gas in California, 2005 (downloaded on Aug. 23, 2019), in 10 pages. URL: http://www.suscon.org/pdfs/cowpower/biomethaneSourcebook/Chapter_4.pdf.

Li et al., "Capturing $CO_2$ from biogas plants", Energy Procedia, Jul. 2017, vol. 114, pp. 6030-6035.

Munoth, K. et al., "Models for Decanting Gaseous Fuel Tanks: Simulations with GFSSP Thermal Model", Mechanical (and Materials) Engineering—Dissertations, University of Nebraska-Lincoln, Dec. 2016, in 133 pages.

Privat, R. et al., "Chapter 15—Predicting the Phase Equilibria of Carbon Dioxide Containing Mixtures Involved in CCS Processes Using the PPR78 Model," $CO_2$ Sequestration and Valorization, Mar. 2014, in 20 pages.

Rufford et al., "The removal of $CO_2$ and $N_2$ from natural gas: A review of conventional and emerging process technologies", Journal of Petroleum Science and Engineering, vol. 94-95, Sep. 2012, pp. 123-154.

Schill, S., "California Carbon Check", Ethanol Producer Magazine, Jan. 23, 2019, in 3 pages. URL: http://www.ethanolproducer.com/articles/15888/california-carbon-check.

Scholwin et al., "Biogas for Road Vehicles: Technology Brief", IRENA Mar. 2017 (Mar. 2017), in 62 pages.

Stafford et al., "Biofuels Technology", United Nations University, Wider Working Paper 2017/87, Apr. 2017, in 25 pages.

Torresani, M. et al., "Renewable Natural Gas Delivery Options. Getting your RNG to Market", Tetra Tech, Mar. 2018, Swanapalooza, Denver, Colorado, in 21 pages.

Unnasch, S., "GHG Emissions Reductions due to the RFS2: A 2018 Update", Life Cycle Associates, Feb. 6, 2019, in 19 pages.

Vitu, S. et al., "Predicting the phase equilibria of $CO_2$ + hydrocarbon systems with the PPR78 model (PR EOS and kij calculated through a group contribution method)", Journal of Supercritical Fluids, May 2008, vol. 45, pp. 1-26.

Wang, Z., "Positioning your plant to maximize the opportunity created by low carbon fuel markets", ACE EcoEngineers, Aug. 16, 2018, in 27 pages.

International Search Report and Written Opinion mailed Mar. 8, 2021 for PCT Application No. PCT/CA2020/051778, filed Dec. 21, 2020.

* cited by examiner

PROCESS AND SYSTEM FOR PRODUCING BIOFUELS WITH REDUCED CARBON INTENSITY

INCORPORATION BY REFERENCE TO ANY PRIORITY APPLICATIONS

N/A.

TECHNICAL FIELD

The present disclosure relates to a process and/or system for producing one or more biofuels with reduced carbon intensity, and in particular, relates to a process and/or system for producing one or more biofuels wherein biogas transported by vehicle is used to reduce the carbon intensity of the biofuel.

BACKGROUND

Concerns over depleting fossil fuel resources and the negative environmental impacts associated with the use of fossil fuels has increased interest in using biomass to produce biofuels and/or other bioproducts (e.g., plastics, fertilizers, lubricants, and/or industrial chemicals). In North America, cars often run on a gasoline/ethanol blend (e.g., E10, E15, or E85), where the ethanol is produced from corn or wheat. Interest in biofuels has been further increased as a result of government initiatives, standards, and/or programs that provide incentives for producing and/or using biofuels (e.g., the Renewable Fuel Standard Program (RFS2) in the United States, the Renewable Energy Directive (RED II) in Europe, the Renewable Transport Fuel Obligation (RTFO) in the United Kingdom, and/or the Low Carbon Fuel Standards (LCFS) in California, Oregon, or British Columbia).

Such programs, which represent an important step in curbing greenhouse gas (GHG) emissions from the transportation sector, may require oil and gas producers to comply each year using appropriate documentation (e.g., that verifies that a certain volume of renewable fuel was produced and/or that verifies that a certain GHG emission reduction was achieved). In some cases, compliance is demonstrated using fuel credits. Fuel credits (e.g., Renewable Identification Numbers (RINs) under the RFS2 or LCFS credits under California's LCFS) may be generated when biofuel is produced. For example, a RIN is a credit that may be generated for each gallon of biofuel (e.g., ethanol, biodiesel, etc.) produced, whereas each LCFS credit represents one metric ton (MT) of carbon dioxide ($CO_2$) reduced. Such fuel credits may be generated, sold, traded, and/or purchased in order to verify compliance with the applicable program.

In some cases, the biofuel must meet a predetermined GHG emission threshold in order to generate fuel credits. For example, to be a renewable fuel under the RFS2, corn ethanol should have lifecycle GHG emissions at least 20% lower than an energy-equivalent quantity of gasoline (e.g., 20% lower than the 2005 EPA average gasoline baseline of 93.08 $gCO_2e/MJ$). In low carbon-related fuel standards, biofuels may be credited according to the carbon reductions of their pathway. For example, under California's LCFS, each biofuel is given a carbon intensity (CI) score indicating their GHG emissions as grams of $CO_2$ equivalent per megajoule of fuel, and fuel credits are generated based on a comparison of their emissions reductions to a target or standard that may decrease each year (e.g., in 2019, ethanol is compared to the gasoline average CI of 93.23 $gCO_2e/MJ$), where lower CIs generate proportionally more credits.

The lifecycle GHG emissions and CI of a biofuel such as ethanol can vary depending upon the feedstock and fuel production process. In a non-limiting example, corn ethanol having a CI of 70 $gCO_2e/MJ$, may have about 20 g/MJ associated with land use change, about 29 g/MJ associated with agriculture (e.g., including the production of fertilizer and soil amendments), about 27 g/MJ associated with biorefining, about 6 g/MJ associated with miscellaneous items such as transporting the feedstock and/or ethanol, and about −12 g/MJ associated with the production of co-products (e.g., distiller's grain and solubles (DGS)). Some factors that affect the CI of ethanol include the feedstock (e.g., corn or sorghum), the type of refining process used (e.g., dry or wet milling), the process fuel used (e.g., natural gas, coal, or biomass), the co-products produced (e.g., wet or dry DGS), and the quantity of electricity purchased from the grid and/or the grid location. For example, since producing dry DGS (DDGS) can require a relatively high amount of energy to dry the DGS, producing wet DGS (WDGS) can typically produce ethanol with a lower CI.

Some approaches proposed to reduce the lifecycle GHG emissions or CI of biofuels, such as ethanol, include using solar power, using biogas, and/or using membrane dehydration. For example, biogas can be produced by an anaerobic digester used to treat waste streams in the ethanol production process (e.g., evaporated condensate, dryer/scrubber streams, thin stillage). Unfortunately, biogas production from these streams may be insufficient to supply the natural gas and/or electricity needs of the process. It has been also proposed to collect biogas produced at a dairy farm and transport it by pipeline to the plant. Unfortunately, this approach may be limited to specific ethanol plants (e.g., located geographically close to the dairy farm) and may also be insufficient to supply the natural gas and/or electricity needs of the process.

SUMMARY

The present disclosure describes a method and/or system for producing one or more fuels (e.g., a biofuel) wherein biogas is transported to the fuel production plant by vehicle (i.e., in a mobile vessel) and is used to produce heat and/or power for producing the fuel.

The biogas, which may be transported as raw biogas, partially purified biogas, or renewable natural gas (RNG), may be compressed to a pressure of at least 1000 psig (6.89 MPa), at least 1500 psig (10.34 MPa), or at least 2000 psig (13.79 MPa), for transport. While compressing biogas to pressures of at least 2000 psig (13.79 MPa) is an energy intensive process that can increase the energy usage of the process and thus may increase the CI of the biofuel (e.g., relative to an analogous case wherein the biogas is transported in a low pressure pipeline and/or is minimally compressed), various embodiments described herein exploit the compressed state of the biogas to reduce net electricity and/or methane usage (i.e., relative to an analogous case wherein the compressed state of the biogas is not exploited) of the fuel production process.

In accordance with one aspect of the instant invention there is provided a process for producing a biofuel comprising: (a) providing biogas from one or more biogas sources, said biogas comprising methane and provided in one or more mobile vessels, each mobile vessel pressurized to at least 2000 psig (13.79 MPa); (b) removing and depressurizing biogas from each of the one or more mobile vessels; (c)

generating heat, power, or a combination thereof, by combusting a gas comprising methane from the biogas removed and depressurized from the one or more mobile vessels; and (d) producing a biofuel or biofuel intermediate in a production process that includes treating a feedstock, said production process including the use of the heat, power, or a combination thereof, generated in step (c), wherein a quantity of biogas used to produce the heat, power, or combination thereof used in step (d) is sufficient to reduce a carbon intensity of the biofuel or biofuel intermediate by at least 5 gCO₂e/MJ, and wherein a change in pressure provided by the depressurizing in step (b) is used to provide work for the production process, cooling for the production process, increased pressure for the production process, or a combination thereof.

In accordance with one aspect of the instant invention there is provided a process for producing one or more biofuels comprising: (a) treating a feedstock to produce one or more sugars; (b) adding a fermentation organism to a mixture comprising the one or more sugars and fermenting the one or more sugars to produce ethanol; (c) recovering the ethanol; (d) removing and depressurizing biogas from one or more mobile vessels pressurized to at least 2000 psig (13.79 MPa), said removed and depressurized biogas comprising methane; (e) generating heat, power, or a combination thereof from at least a portion of the methane; and (f) using the heat, power, or combination thereof in step (a), step (b), step (c), or a combination thereof, thereby reducing a carbon intensity of the ethanol, wherein a change in pressure provided by the depressurizing in step (d) is used to provide (i) work for step (a), step (b), step (c), or a combination thereof, (ii) cooling for step (a), step (b), step (c), or a combination thereof, (iii) increased pressure for step (a), step (b), step (c), or a combination thereof, or (iv) any combination thereof.

In accordance with one aspect of the instant invention there is provided a process for producing one or more biofuels comprising: (a) treating a feedstock to produce one or more sugars; (b) adding a fermentation organism to a mixture comprising the one or more sugars and fermenting the one or more sugars to produce ethanol; (c) recovering the ethanol; (d) removing and depressurizing biogas from one or more mobile vessels having a pressure of at least 2000 psig (13.79 MPa), said removed and depressurized biogas comprising methane; (e) generating heat, power, or a combination thereof from at least some of the methane; (f) using the heat, power, or combination thereof in step (a), step (b), step (c), or a combination thereof, thereby reducing a carbon intensity of the ethanol, wherein said depressurizing comprises providing a pressure drop that cools the removed biogas, and wherein the process comprises providing heat transfer between the cooled biogas and a heat transfer medium and providing cooling for the process with the heat transfer medium.

In accordance with one aspect of the instant invention there is provided a process for producing one or more biofuels comprising: (a) treating a feedstock to produce one or more sugars; (b) adding a fermentation organism to a mixture comprising the one or more sugars and fermenting the one or more sugars to produce ethanol; (c) recovering the ethanol; (d) removing and depressurizing biogas from one or more mobile vessels having a pressure of at least 2000 psig (13.79 MPa), said removed and depressurized biogas comprising methane; (e) generating heat, power, or a combination thereof from at least some of the methane; and (f) using the heat, power, or combination thereof in step (a), step (b), step (c), or a combination thereof, thereby reducing a carbon intensity of the ethanol, wherein said depressurizing the biogas from the one or more mobile vessels comprises providing biogas at a pressure of at least 200 psig (1.38 MPa), wherein generating heat, power, or a combination thereof from at least some of the methane comprises feeding the biogas or a gas derived from the biogas into a gas turbine at a pressure greater than 200 psig (1.38 MPa), and wherein the process is substantially free of significant compression of the biogas removed from the one or more mobile vessels or gas derived from the biogas before being fed to the gas turbine.

DETAILED DESCRIPTION

Figure 1:
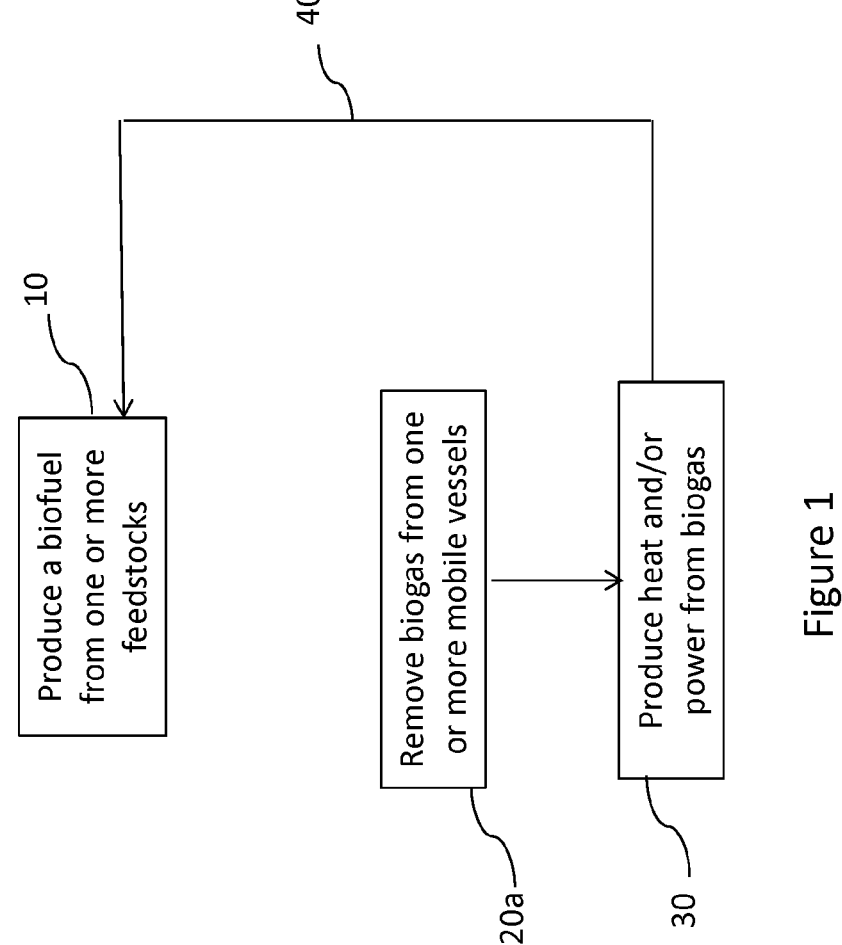
FIG. 1 is a schematic diagram showing a process according to one embodiment wherein raw or partially purified biogas is removed from one or more mobile vessels and combusted to generate heat and/or power for the production of a biofuel.

Certain exemplary embodiments of the invention now will be described in more detail, with reference to the drawings, in which like features are identified by like reference numerals. The invention may, however, be embodied in many different forms and should not be construed as limited to the embodiments set forth herein. The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to."

The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, or the separating of components by the "removal" or "removing" of one component from another, those skilled in the art will understand that the order of addition/removal is not critical (unless stated otherwise). The terms "remove", "removing", and "removal", with reference to one or more impurities, contaminants, and/or constituents of biogas, includes partial removal. The terms "cause" or "causing", as used herein, may include arranging or bringing about a specific result (e.g., a withdrawal of a gas), either directly or indirectly, or to play a role in a series of activities through commercial arrangements such as a written agreement, verbal agreement, or contract. The term "associated with", as used herein with reference to two elements (e.g., a fuel credit associated with the transportation fuel), is intended to refer to the two elements being connected with each other, linked to each other, related in some way, dependent upon each other in some way, and/or in some relationship with each other. The terms "first", "second", etc., may be used to distinguish one element from another, and these elements should not be limited by these terms. The term "plurality", as used herein, refers to two or more. Unless defined otherwise, all technical and scientific terms used herein have the same meanings as commonly understood by one of ordinary skill in the art.

Referring to FIG. 1, there is shown an embodiment of the invention, wherein a process for producing one or more biofuels includes the steps of producing a biofuel from one or more feedstocks 10, removing biogas from one or more mobile vessels 20*a*, and using the removed biogas to provide heat (e.g., steam) and/or power (e.g., electricity) 30 for the fuel production process 10. Advantageously, since at least a portion of the heat and/or power used for the fuel production process 10 is produced from biogas, the carbon intensity (CI) of the biofuel can be reduced (i.e., relative to the case where that portion of the heat and/or power was produced from fossil fuels). In one embodiment, the biogas removed from the one or more mobile vessels 20*c* is raw biogas, partially purified biogas, and/or RNG. In one embodiment, the biogas removed from the one or more mobile vessels 20*c* is raw biogas and/or partially purified biogas.

While using biogas to reduce the CI of a biofuel is known, the approaches proposed typically produce raw biogas on site (e.g., with one or more anaerobic digesters) or transport raw biogas over short distances by pipeline (i.e., to the site). Such approaches are compatible with the relatively low economic value of raw biogas (i.e., relative to natural gas) and with the fact that raw biogas typically has a relatively high $CO_2$ content, which can make it more challenging to transport (e.g., economically and/or technically). In contrast, in the embodiment described in FIG. 1, the biogas is provided in one or more mobile vessels, and thus can be transported by vehicle (e.g., truck). In one embodiment, the biogas removed from the one or more mobile vessels 20*a* is pressurized to at least 1000 psig (6.89 MPa), at least 1500 psig (10.34 MPa), or at least 2000 psig (13.79 MPa). In one embodiment, removing the biogas from the one or more mobile vessels includes depressurizing the biogas. In one embodiment, the biogas in the one or more mobile vessels is pressurized to at least 2000 psig (13.79 MPa), and the process includes depressurizing the biogas using a depressurization method that reduces utility requirements (i.e., electricity and/or natural gas) of the production process 10 per unit of biofuel produced, relative to an analogous process where the depressurization method is not used to reduce utility requirements. In one embodiment, the biogas in the one or more mobile vessels is pressurized to at least 2000 psig (13.79 MPa), and the process includes depressurizing the biogas using a depressurization method that reduces the process energy requirements per unit of biofuel. In general, pressurizing the biogas to at least 2000 psig (13.79 MPa) in the one or more mobile vessels requires significant energy. The energy introduced by the pressurization can be stored in and/or recovered from the high-pressure gas and used in the fuel production process 10. In one embodiment, at least a portion of the latent energy of the compressed biogas is harnessed to provide work (e.g., electricity or to drive rotary equipment), to provide cooling, and/or to provide increased pressure for the fuel production process 10. In one embodiment, removing the biogas from the one or more mobile vessels decreases the enthalpy of the biogas, and the process includes recovering enthalpy from the decompression for use in the process (e.g., by providing work and/or cooling). In one embodiment, removing the biogas from the one or more mobile vessels decreases the enthalpy of the biogas, and depressurization is controlled such that the enthalpy of the depressurized biogas used to produce the heat and/or power is higher than the enthalpy of an equivalent amount of natural gas (i.e., in energy content) provided from a commercial distribution system connected to the fuel production facility (e.g., at a pressure less than 30 psig (0.21 MPa), less than 20 psig (0.14 MPa), or less than 10 psig (0.07 MPa)). In one embodiment, removing the biogas from the one or more mobile vessels includes providing a change in pressure used to provide work, cooling, and/or increased pressure that is used in the fuel production process 10.

Figure 2:
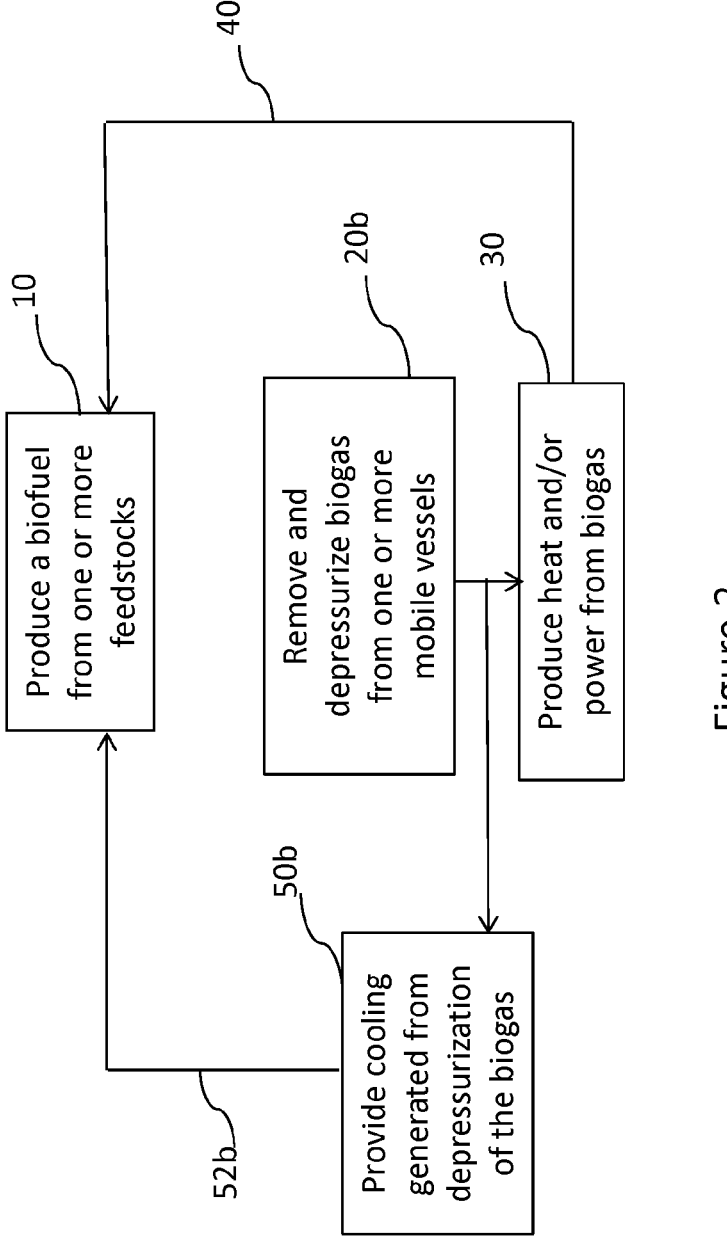
FIG. 2 is a schematic diagram showing a process according to one embodiment wherein biogas is removed from one or more mobile vessels and depressurized, and wherein cooling produced by the depressurization is used in the production of a biofuel.

Referring to FIG. 2, there is shown an embodiment of the invention, wherein a process for producing one or more biofuels includes the steps of producing a biofuel from one or more feedstocks 10, removing and depressurizing biogas from one or more mobile vessels 20*b*, and using the biogas removed from the one or more mobile vessels to provide heat (e.g., steam) and/or power (e.g., electricity) 30 for the fuel production process 10. Advantageously, since at least a portion of the heat and/or power used for the fuel production process 10 is produced from biogas, the lifecycle GHG emissions of the biofuel can be reduced (i.e., relative to the case where that portion of the heat and/or power was produced from fossil fuels). In this embodiment, the biogas that is removed from the one or more mobile vessels 20*b* is raw biogas, partially purified biogas, or RNG, and is depressurized using a depressurization method wherein a temperature of the removed biogas is reduced (e.g., as the biogas is expanded it is cooled as a result of the Joule Thomson effect). In one embodiment, the temperature drop provided by the pressure change is used to provide cooling for the fuel production process 10. In one embodiment, the process includes providing heat transfer between the cooled biogas and a heat transfer medium 50*b*, and using the heat transfer medium to provide cooling 52*b* in the fuel production process 10, thereby reducing the process energy requirements per unit of biofuel (e.g., less electricity is required for process chilling since cold is provided from the depressurization). In one embodiment, the lower temperature provided by the depressurization is used to cool a circulating fluid that provides cooling within the fuel production process 10. One approach to providing cooling in fuel production processes (e.g., oil refining, corn ethanol, etc.) is to use a cooling tower, wherein circulating water warmed by the process is cooled as it cascades over baffles (or fill), which promotes evaporation. While widely used, cooling towers unfortunately can increase water usage of the fuel production process. However, by using the temperature drop provided by depressurization, water usage of the fuel production process does not significantly increase as a result of the cooling process. Moreover, it is not limited by ambient temperatures. Advantageously, using the temperature drop provided by depressurization to decrease the temperature of a circulating water (e.g., warmed by the fuel production process) also increases the temperature of the removed biogas. Since biogas provided at relatively low temperatures (e.g., below about −20° C., below about −25° C., below about −40° C., or below about −50° C.) can need to be reheated before further processing and/or combustion (e.g., to reduce risks of line freezing and/or damage to equipment), this can reduce costs associated with heating the cooled biogas.

Figure 3:
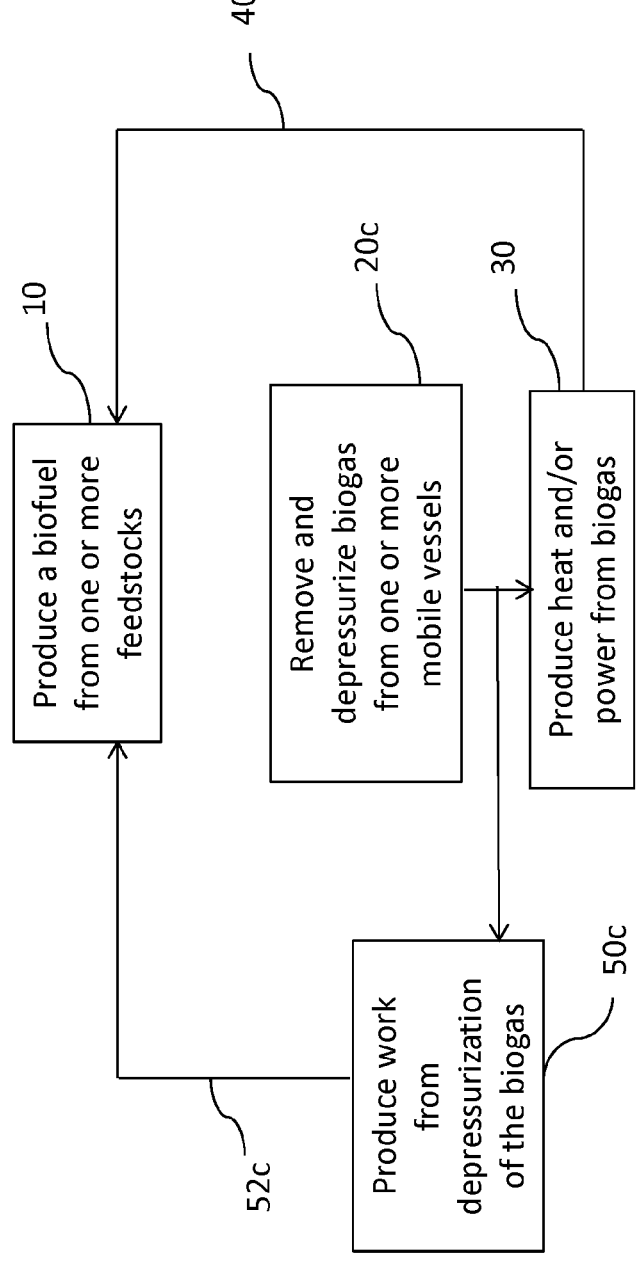
FIG. 3 is a schematic diagram showing a process according to one embodiment wherein biogas is removed from one or more mobile vessels and depressurized, and wherein work produced by the depressurization is used in the production of a biofuel.

Referring to FIG. 3, there is shown an embodiment of the invention, wherein a process for producing one or more biofuels includes the steps of producing a biofuel from one or more feedstocks 10, removing and depressurizing biogas from one or more mobile vessels 20c, and using the biogas removed from the one or more mobile vessels to provide heat (e.g., steam) and/or power (e.g., electricity) 30 for the fuel production process 10. Advantageously, since at least a portion of the heat and/or power used for the production process 10 is produced from biogas, the lifecycle GHG emissions of the biofuel can be reduced (i.e., relative to the case where that portion of the heat and/or power was produced from fossil fuels). In this embodiment, the biogas that is removed from the one or more mobile vessels 20c is raw biogas, partially purified biogas, or RNG, and is depressurized using a depressurization method that produces work for the fuel production process (e.g., using a turboexpander). In one embodiment, the change in pressure from the depressurization is sufficient to drive the shaft of a turboexpander that is coupled to a generator (e.g., for generating electricity) or another piece of equipment (e.g., a compressor, blower, etc.). In one embodiment, the process includes generating electricity using the turboexpander 50c, and using the electricity generated in the production process 10 (e.g., to drive equipment in the process), thereby reducing energy requirements per unit of biofuel. In one embodiment, the process includes using the turboexpander 50c to drive one or more pieces of equipment (e.g., blower, pump, milling equipment, etc.), thereby reducing the energy requirements per unit of biofuel. In one embodiment, the biogas is removed from the one or more mobile vessels such that the pressure of the biogas removed from the one or more vessels is substantially constant (and relatively high) as it is fed to the turboexpander (e.g., using a positive displacement method wherein the biogas is displaced from the mobile vessel(s) using a liquid or piston).

Figure 4:
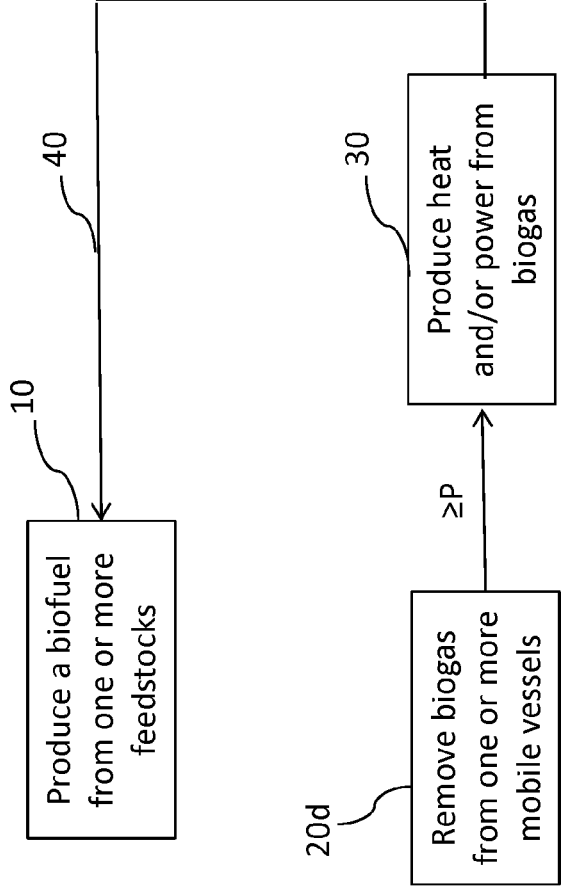
FIG. 4 is a schematic diagram showing a process according to one embodiment wherein biogas is removed from one or more mobile vessels and depressurized, and wherein increased pressure provided by the depressurization is used in the production of a biofuel.

Referring to FIG. 4, there is shown an embodiment of the invention, wherein a process for producing one or more biofuels includes the steps of producing a biofuel from one or more feedstocks 10, removing and depressurizing biogas from one or more mobile vessels 20d, and using the biogas removed from the one or more mobile vessels to provide heat (e.g., steam) and/or power (e.g., electricity) 30 for the fuel production process 10. Advantageously, since at least a portion of the heat and/or power used for the fuel production process 10 is produced from biogas, the lifecycle GHG emissions of the biofuel can be reduced (i.e., relative to the case where that portion of the heat and/or power was produced from fossil fuels). In this embodiment, the biogas is raw biogas, partially purified biogas, or RNG, and removing and depressurizing the biogas 20d includes depressurizing the biogas from a first pressure to a second pressure P, where the second pressure P is at least 100 psig (0.69 MPa). For example, in one embodiment, the second pressure P is at least 150 psig (1.03 MPa), at least 200 psig (1.38 MPa), at least 300 psig (2.07 MPa), 400 psig (2.76 MPa), 500 psig (3.45 MPa), 600 psig (4.14 MPa), 700 psig (4.83 MPa), 800 psig (5.52 MPa), 900 psig (6.20 MPa), 1000 psig (6.89 MPa), 1100 psig (7.58 MPa), or at least 1200 psig (8.27 MPa). Biogas (i.e., raw, partially purified, or fully upgraded) at the second pressure P is combusted to produce heat and/or power 30. In some cases, combustion units used to produce heat and/or power can function more efficiently with high fuel input pressures. For example, a gas turbine may operate with fuel pressures of about 180 psig (1.24 MPa) or higher (e.g., between 580 to 1020 psig), and thus may require that the fuel be fed to an upstream compressor. In the embodiment illustrated in FIG. 4, the relatively high pressure of the biogas in the one or more mobile vessels is exploited to avoid, or reduce, compression of the biogas before it is combusted. For example, in one embodiment, the one or more mobile vessels are only depressurized to a pressure that corresponds approximately to the fuel input pressure recommended for the combustion unit, thereby reducing compression requirements for the combustion (e.g., relative to if the biogas was transported by pipeline at a pressure under 80 psig (0.55 MPa)), thereby reducing the process energy requirements per unit of biofuel.

Figure 5:
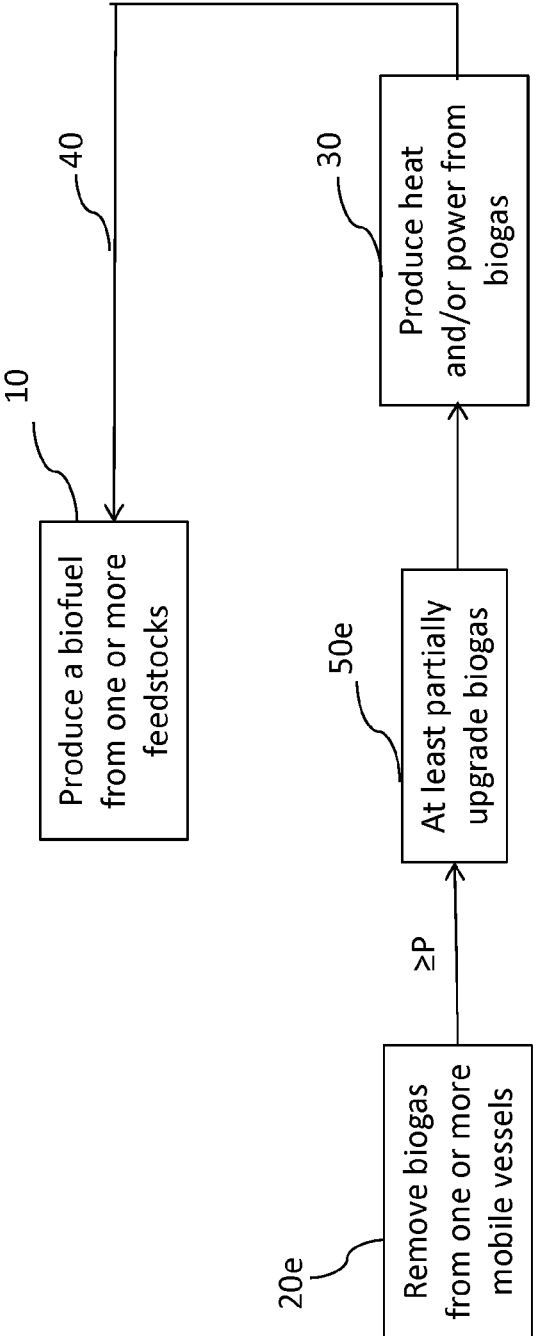
FIG. 5 is a schematic diagram showing a process according to one embodiment wherein biogas is removed from one or more mobile vessels, depressurized, and subjected to a biogas upgrading, and wherein increased pressure provided by the depressurization is used in the production of a biofuel.

Referring to FIG. 5, there is shown an embodiment of the invention, wherein a process for producing one or more biofuels includes the steps of producing a biofuel from one or more feedstocks 10, removing and depressurizing biogas from one or more mobile vessels 20e, and using the biogas removed from the one or more mobile vessels to provide heat (e.g., steam) and/or power (e.g., electricity) 30 for the fuel production process 10. Advantageously, since at least a portion of the heat and/or power used for the fuel production process 10 is produced from biogas, the lifecycle GHG emissions of the biofuel can be reduced (i.e., relative to the case where that portion of the heat and/or power was produced from fossil fuels). In this embodiment, the biogas is raw biogas and/or partially purified biogas, and removing and depressurizing the biogas 20d includes depressurizing the biogas from a first pressure to a second pressure P, where the second pressure is at least 100 psig (0.69 MPa). For example, in one embodiment, the second pressure is at least 200 psig (1.38 MPa), at least 300 psig (2.07 MPa), 400 psig (2.76 MPa), 500 psig (3.45 MPa), 600 psig (4.14 MPa), 700 psig (4.83 MPa), 800 psig (5.52 MPa), 900 psig (6.20 MPa), 1000 psig (6.89 MPa), 1100 psig (7.58 MPa), or at least 1200 psig (8.27 MPa). Biogas (i.e., raw or partially purified) at the second pressure P is fed to a biogas upgrading system wherein it is at least partially upgraded 50e, and the at least partially upgraded biogas is then combusted to generate heat and/or electricity 30. In this embodiment, the biogas upgrading system requires an input gas feed that is at an elevated pressure (i.e., at least 200 psig) in order to function efficiently. In one embodiment, the upgraded biogas is then depressurized and fed to the combustion unit. In one embodiment, the biogas upgrading system is configured to operate substantially at this elevated pressure P and to provide an upgraded biogas at a pressure that is at least 200 psig, at least 300 psig (2.07 MPa), at least 400 psig (400 psig), at least 500 psig (3.45 MPa), at least 600 psig, at least 700 psig (4.83 MPa), at least 800 psig (5.52 MPa), at least 900 psig (6.20 MPa), or at least 1000 psig (6.89 MPa), without substantial compression. By reducing compression requirements after the biogas has been transported to the fuel production facility, energy requirements per unit of biofuel are reduced.

In each of these embodiments, the relatively high pressure of the biogas in the one or more mobile vessels (e.g., raw, partially purified, and/or RNG) can be exploited to reduce energy requirements of the fuel production process (e.g., reduce utilities), thereby recovering some of the energy used to compress the biogas when filling the one or more mobile vessels. This offset may be particularly important when the biogas is provided to reduce the lifecycle GHG emissions of the biofuel. For example, if the carbon emissions associated with biogas production (e.g., including those for compressing and transporting the biogas) is higher than the GHG reductions achieved by displacing natural gas, then the lifecycle GHG emissions of the product may not be reduced.

In each of these embodiments, at least some of the biogas for the production process 10 is provided in one or more mobile vessels. Accordingly, at least some of the biogas may be provided from one or more biogas sources that are not physically connected by pipeline to the fuel production facility (although in some embodiments the fuel production facility may also include and/or be connected to one or more sources of biogas). While compressing biogas and transporting it in a mobile vessel may result in additional GHG emissions (e.g., relative to transporting it by pipeline), the net GHG emissions for the biofuel can be reduced with the selection of suitable amounts and types of biogas (e.g., different biogas sources). For example, while upgraded landfill gas may have a carbon intensity (CI) of about 40-50 $gCO_2e/MJ$, biogas produced from manure is typically lower (e.g., dairy manure may have CI of about −270 $gCO_2e/MJ$, while swine manure may have a CI that is about −350 $gCO_2e/MJ$). Providing a delivery system that includes transporting biogas in one or more mobile vessels allows biogas to be collected from multiple farms (e.g., dairy or swine) that otherwise could be emitted to the atmosphere and/or flared.

Figure 6:
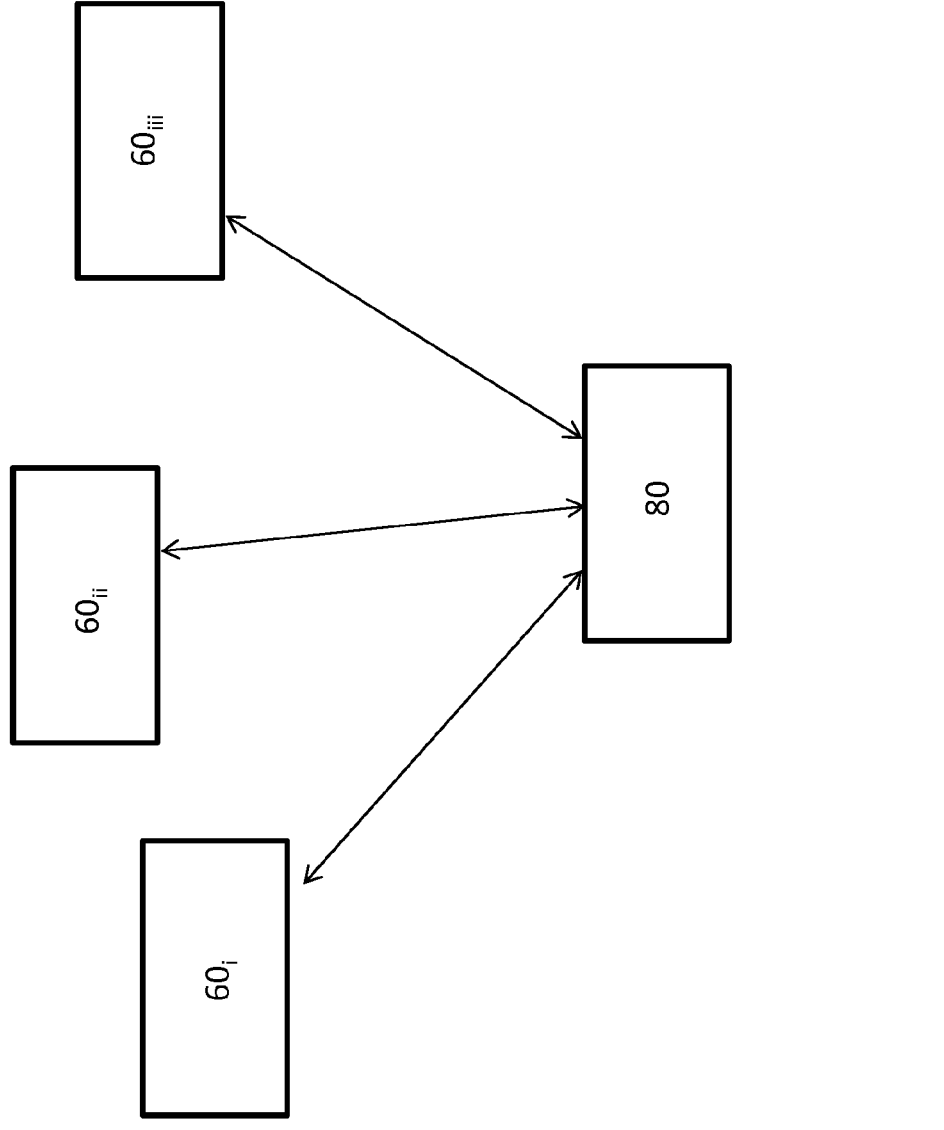
FIG. 6 is a schematic diagram showing one embodiment of a configuration used to provide biogas from a plurality of biogas sources.

In one embodiment, the biogas removed from the one or mobile vessels is provided using a delivery system wherein biogas from a plurality of biogas sources is transported to a receiving station 80 (e.g., as illustrated in FIG. 6). More specifically, biogas from each biogas source 60i, 60ii, 60iii, is compressed in a respective mobile vessel and is transported directly to the receiving station 80, where it can be removed and depressurized, and used to provide heat and/or power for the fuel production process 10. In one embodiment, the receiving station includes connecting means (e.g., high pressure piping, tubing, flexible hose, manifold(s), switching valves, couplings, etc.) for connecting to the one or more mobile vessels. In one embodiment, the receiving station includes a plurality of docks, each of which is designed to accommodate a different mobile vessel or truck supporting one or more mobile vessels. In one embodiment, the receiving station includes a plurality of docking stations, each of which can accommodate a trailer, skid, or shipping container. In one embodiment, the receiving station includes a pressure let down system. In one embodiment, the receiving station is located at the fuel production facility. In one embodiment, the receiving station is located at a processing site connected to a plurality of farms by pipeline.

In one embodiment, the delivery system includes one or more trucks fueled by biogas, partially purified biogas, or RNG. In one embodiment, the delivery system includes one or more trucks fueled by bio-CNG or bio-LNG.

In one embodiment, the biogas from each biogas source is transported as raw biogas. In one embodiment, the biogas from each biogas source is transported as partially purified biogas. In one embodiment, the biogas from each biogas source is transported as RNG. In one embodiment, the biogas provided in different mobile vessels has different purities (e.g., different methane contents). In one embodiment, the biogas from one biogas source is transported as raw biogas, while biogas from another biogas source is transported as partially purified biogas or RNG.

In one embodiment, the fuel production process produces a single biofuel or biofuel intermediate (e.g. ethanol, DME, diesel having renewable content, methanol, etc.). In one embodiment, the fuel production process produces a plurality of biofuels and/or fuel intermediates. In one embodiment, the fuel production process produces ethanol and RNG. In one embodiment, the fuel production process produces at least one biofuel or biofuel intermediate other than RNG.

Biogas Production

For purposes herein, the term "biogas", which refers to a gas mixture that contains methane produced from the anaerobic digestion of organic matter, encompasses raw biogas, partially purified biogas, and renewable natural gas (RNG), unless otherwise specified. Raw biogas refers to biogas before it is treated to remove any chemical components (e.g., $CO_2$, $H_2S$, $H_2O$, $N_2$, $NH_3$, $H_2$, CO, $O_2$, VOCs, and/or siloxanes). The term "partially purified biogas" refers to biogas that has been treated to remove non-methane components (e.g., $CO_2$, $H_2S$, $H_2O$, $N_2$, $NH_3$, $H_2$, CO, $O_2$, VOCs, and/or siloxanes), but requires further purification in order to meet pipeline specifications (e.g., it may contain one or more non-methane components in an amount that causes it to fall short of meeting natural gas pipeline standards or specifications). The term "renewable natural gas" or "RNG" refers to biogas that has been upgraded to meet or exceed applicable natural gas pipeline quality standards and/or specifications, meet or exceed applicable quality specifications for vehicle use (e.g., CNG specifications), and/or that qualifies as RNG under applicable regulations. Pipeline specifications include specifications required for biogas for injection into a natural gas commercial distribution system. Pipeline quality standards or specifications may vary by region and/or country in terms of value and units. For example, pipelines standards may require the RNG to have a $CH_4$ level that is at least 95% or have a heating value of at least 950 BTU/scf.

In general, the biogas provided in the one or more mobile vessels may include biogas from any suitable source. For example, the biogas may be obtained from a landfill and/or from one or more anaerobic digesters. In embodiments where the biogas is obtained from one or more anaerobic digesters, the digesters may be connected in series and/or in parallel, may be single-stage or multi-stage digestion systems, and/or may be designed and/or operated in a number of configurations including batch or continuous, mesophilic or thermophilic temperature ranges, and low, medium, or high rates. In addition, in embodiments where the biogas is obtained from one or more anaerobic digesters, the digesters may be used for manure or other farm waste, for wastewater treatment, for treating industrial waste, and/or for treating wastewater, wastes, and/or residues from an ethanol process.

In one embodiment, the biogas is sources from one or more anaerobic digesters fed manure. In one embodiment, the biogas is sourced from one or more manure-fed anaerobic digesters at a dairy farm. In one embodiment, the biogas is sourced from one or more manure-fed anaerobic digesters at a swine farm. In one embodiment, the biogas is sourced from a landfill site. In one embodiment, the biogas is sourced from a wastewater treatment plant (WWTP). In one embodiment, the biogas is sourced from one or more anaerobic digesters processing manure and/or from a landfill.

Raw biogas may, for example, have a methane ($CH_4$) content between about 35% and 75% (e.g., average of about 60%) and a carbon dioxide ($CO_2$) content between about 15% and 65% (e.g., average of about 35%), depending on the source. For example, without being limiting, biogas from anaerobic digesters fed agricultural waste may have a methane content between about 50% and 75%, whereas biogas from a landfill site may have a methane content between about 25% and 65%. In one embodiment, the raw biogas has a methane content between about 25% and 75% and a carbon dioxide content between about 15% and 65%, and the carbon dioxide and methane make up at least 75% of the biogas by volume.

In one embodiment, each biogas source (e.g., based on landfill or anaerobic digester) produces raw biogas at a rate less than 6000 SCFM (standard cubic feet per minute). In one embodiment, the biogas source produces raw biogas at a rate less than 5000 SCFM. In one embodiment, the biogas source produces raw biogas at a rate between 100 and 3000 SCFM. In one embodiment, the biogas source produces raw biogas at a rate between 1000 and 3000 SCFM. In one embodiment, the biogas source produces raw biogas at a rate between 1500 and 3000 SCFM.

The percentages used to quantify gas composition and/or a specific gas content, as used herein, are expressed as mol %, unless otherwise specified.

Partial Purification and/or Biogas Upgrading

In general, the biogas provided from each biogas source may be purified before and/or after transport by mobile vessel.

In one embodiment, the biogas from each source is partially purified at a processing site at or close to the corresponding biogas source 60i, 60ii, 60iii (e.g., before transport in the mobile vessel). In one embodiment, the partial purification removes $H_2O$, $H_2S$, and/or $CO_2$ from the raw biogas to provide partially purified biogas having a $H_2O$ content, $H_2S$ content, and/or $CO_2$ content that is less than that of the raw biogas. Optionally, one or more other non-methane components are removed.

In embodiments where the biogas is partially purified at each processing site, the partial purification does not produce a gas that meets applicable quality specifications for injection into the natural gas distribution system (e.g., pipeline standards) and/or is suitable for use in the transportation sector, but rather, requires further purification in order to qualify as RNG under applicable regulations. For example, in one embodiment, the partially purified biogas has a non-methane content of at least 20%, at least 15%, at least 12%, at least 10%, at least 8%, at least 6%, or at least 5%. In one embodiment, the partially purified biogas has an inert content (e.g., $CO_2$, $N_2$, helium, argon, neon) that is greater than 10%.

In one embodiment, the partially purified biogas has a $CO_2$ content less than 10%, less than 9%, less than 8%, less than 7%, less than 6%, or less than 5%. In one embodiment, the partially purified biogas has a $CO_2$ content between about 4% and 8%, between about 4% and 9%, or between about 4% and 10%. In one embodiment, the partially purified biogas has a $CH_4$ content between about 50% and about 93%. In one embodiment, the partially purified biogas has a $CH_4$ content between about 50% and about 90% and an $N_2$ content between about 10% and 20%. In one embodiment, the partially purified biogas has a $CH_4$ content between about 80% and about 90% and an $N_2$ content between about 10% and 20%. In one embodiment, the partially purified biogas has a $CH_4$ content between about 72% and about 90%, a $CO_2$ content between about 0 and 8%, and an $N_2$ content between about 5% and 20%. In one embodiment, the partially purified biogas has a combined $CH_4$ and $N_2$ content that is greater than 98%, where the $N_2$ content is at least 5%. In one embodiment, the partially purified biogas has a combined $CH_4$ and $N_2$ content that is greater than 98%, and a $CO_2$ content that is less than 1%. In one embodiment, the partially purified biogas has a combined $CH_4$ and $N_2$ content that is greater than 98%, where the $N_2$ content is at least 5%, and wherein the $CO_2$ content is less than 200, 100, 50, or 30 ppm.

In one embodiment, the partially purified biogas has a non-methane content that is at least 50%, at least 55%, at least 60%, at least 65%, or at least 70%. In one embodiment, the partially purified biogas has a non-methane content that is greater than 60%. In one embodiment, the partially purified biogas has a non-methane content between 50% and 60%. In one embodiment, less than 5%, less than 10%, less than 15%, or less than 20% of the $CO_2$ present in the raw biogas is removed in the partial purification.

In one embodiment, the partial purification of the raw biogas is provided using a stationary purification system (e.g., installed at the processing site). Using a stationary purification system advantageously allows the partial purification system to be readily available on-site to at least partially purify the raw biogas as it is produced. Moreover, since the purification system is stationary it can be designed and/or selected in dependence upon the average composition of the raw biogas from that particular source. Furthermore, since the purification system remains on-site (e.g., is not transported with the vessels) more partially purified biogas may be transported. For purposes herein, the term "stationary" as used with reference to a purification system, refers to the purification system not moving from the pre-processing site or facility at which it is used (although it may move within the processing site or facility).

In one embodiment, at least part of the partial purification is achieved using a stationary purification system based on any suitable method/technology, or combination of methods/technologies, in one or more stages, as known in the art. For example, $H_2O$ may be removed using a standard biogas dehumidifier, whereas $H_2S$ may be removed using a commercial $H_2S$ removal unit (e.g., based on activated carbon, molecular sieve, iron sponge, water scrubbing, NaOH washing, and/or biofilter or biotrickling filter technologies). In one embodiment, the partial purification system includes a dehumidifier, a scrubber, a membrane unit, a solvent extraction unit, a pressure swing adsorption unit, and/or a cryogenic unit.

In one embodiment, the partial purification is essentially a cleaning or pre-cleaning stage that does not significantly remove $CO_2$ or $N_2$. For example, in one embodiment, the partial purification removes $H_2O$ and/or $H_2S$, but does not significantly remove $CO_2$ or $N_2$.

In one embodiment, the partial purification removes $H_2O$. Raw biogas may be fully saturated with water vapour and/or may have a water content of about 7% (at 40° C.). Removing $H_2O$ is advantageous since moisture can condense into water or ice when passing from high to low pressure systems, which may cause corrosion, may result in clogging, and/or may interfere with gas flow and pressure measurements (e.g., causing system control problems). In addition, the presence of water may cause hydrates to form. In one embodiment, the partial purification removes more than 90%, 92%, 94%, 96%, or 98% of the $H_2O$ present in the raw biogas. In one embodiment, the partial purification removes more than 99% of the $H_2O$ present in the raw biogas. In one embodiment, the partial purification removes sufficient $H_2O$ from the raw biogas that the $H_2O$ content of partially purified biogas meets or exceeds the $H_2O$ content specifications for RNG. In one embodiment, the partial purification 20 does not remove $H_2O$. In one embodiment, the partial purification removes sufficient moisture to provide the partially purified biogas with an $H_2O$ concentration of less than 0.4 $g/m^3$ of biogas. In one embodiment, the partial purification removes sufficient moisture to provide the partially purified biogas with an $H_2O$ concentration of less than 0.2 $g/m^3$ of biogas. In one embodiment, the partial purification includes an $H_2O$ removal stage that uses refrigeration techniques or desiccant drying. In one embodiment, the partial purification includes multi-stages of $H_2O$ removal (e.g., first stage of $H_2O$ removal followed by a second stage of $H_2O$ removal), which may or may not be consecutive.

In one embodiment, the partial purification removes $H_2S$. Raw biogas may have an $H_2S$ concentration between about 0 and about 6700 ppm(v) (e.g., 0-10,000 $mg/m^3$). For example, without being limiting, biogas derived from agricultural waste may have an $H_2S$ concentration between 0-4000 ppm(v), whereas biogas from a landfill may have an $H_2S$ concentration between 0 and 1000 ppm(v). $H_2S$ is both poisonous and corrosive, and can damage piping, equipment, and instrumentation. $H_2S$ can be reactive with many metals, and the reactivity can be higher at higher concentration and pressure, and/or in the presence of water. In one embodiment, the partial purification removes more than 90%, 92%, 94%, 96%, or 98% of the $H_2S$ present in the raw biogas. In one embodiment, the partial purification removes more than 99% of the $H_2S$ present in the raw biogas. In one embodiment, the partial purification removes sufficient $H_2S$ from the raw biogas that the $H_2S$ content of partially purified biogas meets or exceeds the $H_2S$ content specifications for RNG. In one embodiment, the partial purification removes sufficient $H_2S$ from the raw biogas that the $H_2S$ content of partially purified biogas is safer to transport but requires additional $H_2S$ removal to meet RNG standards. In one embodiment, the partial purification does not remove $H_2S$. In one embodiment, the partial purification removes sufficient $H_2S$ from the raw biogas that the $H_2S$ concentration of partially purified biogas is less than 200 ppm(v). In one embodiment, the partial purification removes sufficient $H_2S$ from the raw biogas that the $H_2S$ concentration of partially purified biogas is less than 100 ppm(v). In one embodiment, the partial purification removes sufficient $H_2S$ from the raw biogas that the $H_2S$ concentration of partially purified biogas is between 20 ppm(v) and 50 ppm(v). In one embodiment, the partial purification removes sufficient $H_2S$ from the raw biogas that the $H_2S$ concentration of partially purified biogas is less than 50, 40, 30, 20, or 10 ppm(v). In one embodiment, the partial purification removes sufficient $H_2S$ from the raw biogas that the $H_2S$ concentration of partially purified biogas is less than about 6 ppm(v). In one embodiment, the partial purification includes a first stage of $H_2S$ removal (e.g., biological) followed by second stage of $H_2S$ removal (e.g., an adsorption bed), which may or may not be consecutive.

In one embodiment, the partial purification removes $H_2O$ and $H_2S$. Contaminants such as $O_2$, $NH_3$, VOCs, siloxanes, and/or particulates are optionally removed, although this is not necessary. Although the fuel production process 10 may include $H_2O$ and/or $H_2S$ removal (e.g., to protect the combustion system), it can be advantageous to remove $H_2O$ and/or $H_2S$ prior to collection and/or transport. For example, transporting gas with $H_2S$ creates the risk that in the event of a leak or accident, $H_2S$ leaks out, thereby creating toxic gas and safety issues. This risk is eliminated or reduced when the partial purification includes $H_2S$ removal.

In addition, since $H_2S$, and in particular the combination of $H_2O$ and $H_2S$, can cause corrosion problems, removing the $H_2O$ and/or $H_2S$ can reduce equipment maintenance costs, and provide flexibility on construction materials for mobile vessels. Furthermore, removing $H_2S$ may improve the $CO_2/CH_4$ separation if present during the partial purification. Removing water may reduce the risk of hydrate formation.

In one embodiment, the partial purification removes $O_2$. Removing $O_2$ may be particularly advantageous prior to compression and transport.

In one embodiment, the partial purification removes $CO_2$. In one embodiment, the partial purification removes $CO_2$ and/or $N_2$. Contaminants such as $H_2O$, $H_2S$, $O_2$, $NH_3$, VOCs, siloxanes, and/or particulates are optionally removed. For example, some $CO_2$ removal technologies also remove $H_2S$. Even removing half of the $CO_2$ present in biogas can significantly reduce the amount of gas that needs to be compressed and/or transported. For example, transporting partially purified biogas, particularly when $CO_2$ has been removed, is generally more efficient (e.g., in terms of both costs and GHG emission reductions) than transporting raw biogas. In addition, the $CO_2$ in raw biogas can make it more challenging (e.g., there can be phase change issues when $CO_2$ is compressed or depressurized) and/or less energy efficient to compress relative to pure $CH_4$.

In one embodiment, the partial purification removes more than 90%, 92%, 94%, 96%, or 98% of the $CO_2$ present in the raw biogas. In one embodiment, the partial purification removes more than 20%, 30%, 40% or 50% of the $CO_2$ present in the raw biogas. In one embodiment, the partial purification removes between about 5% and 20% of the $CO_2$ present in the raw biogas. In one embodiment, the partial purification removes less than 5% of the $CO_2$ present in the raw biogas. In one embodiment, the partial purification does not substantially remove $CO_2$. In one embodiment, no more than 75% of the $CO_2$ is removed.

In one embodiment, the partial purification removes sufficient $CO_2$ to increase the heating value of the biogas by at least 50 BTU/scf, at least 100 BTU/scf, at least 150 BTU/scf, at least 200 BTU/scf, or at least 250 BTU/scf. For example, in one embodiment, the partial purification increases the heating value of the biogas (e.g., which may be about 350-500 BTU/scf) to at least 600 BTU/scf, at least 700 BTU/scf, or at least 800 BTU/scf, but retains sufficient $CO_2$ and/or $N_2$ such that the heating value does not exceed 900 BTU/scf, 925 BTU/scf, or 950 BTU/scf. The term "heating value", as used herein, refers to the higher heating value (HHV), unless otherwise specified.

In one embodiment, the partial purification removes sufficient $CO_2$ from the raw biogas that the $CO_2$ content of partially purified biogas is less than 25%. In one embodiment, the partial purification removes sufficient $CO_2$ from the raw biogas that the $CO_2$ content of partially purified biogas is less than 20%, 15%, 10%, or 8%. In one embodiment, the partial purification removes sufficient $CO_2$ from the raw biogas that the $CO_2$ content of partially purified biogas is less than 5%. In one embodiment, the partial purification removes sufficient $CO_2$ from the raw biogas that the $CO_2$ content of partially purified biogas is less than 4%.

In one embodiment, the partial purification removes between 10% and 85% of the $CO_2$. In one embodiment between 20% and 80% of the $CO_2$ is removed. In one embodiment between 40% and 60% of the $CO_2$ is removed. In one embodiment between 84% and 90% of the $CO_2$ is removed. In one embodiment, the partial purification system used removes more than 10% and less than 95% of the $CO_2$ in the biogas. For example, removing 10% of the $CO_2$ from a biogas containing 50% $CH_4$, 38% $CO_2$, 10% $N_2$, and 2% $O_2$, provides a partially purified biogas containing 52% $CH_4$, 35.6% $CO_2$, 10.4% $N_2$, and 2.1% $O_2$, whereas removing 85% of the $CO_2$ from the biogas containing 50% $CH_4$, 38% $CO_2$, 10% $N_2$, and 2% $O_2$, provides a partially purified biogas containing 73.9% $CH_4$, 8.4% $CO_2$, 14.8% $N_2$, and 3% $O_2$. Removing only enough $CO_2$ to yield a partially purified biogas having a $CH_4$ content that is less than 85% is advantageous in that such upgrading is relatively easy and/or can be achieved using commercial systems that are less costly. In one embodiment, sufficient $CO_2$ is removed so as to provide the partially purified biogas with a $CH_4$ content that is at least 70% and no more than 90%, which may provide a good balance between upgrading cost and compressibility.

In one embodiment, the relative high pressures required for transport are used to improve the partial purification. In one embodiment, at least one stage of the partial purification is conducted at a pressure of at least 100 psig (0.69 MPa), of at least 200 psig (1.38 MPa), of at least 300 psig (2.07 MPa), of at least 400 psig (2.76 MPa), of at least 500 psig (3.45 MPa), of at least 600 psig (4.14 MPa), of at least 700 psig (4.83 MPa), or of at least 800 psig. In one embodiment, the partial purification provides partially purified biogas at a pressure of at least 100 psig (0.69 MPa), of at least 200 psig (1.38 MPa), of at least 300 psig (2.07 MPa), of at least 400 psig (2.76 MPa), of at least 500 psig (3.45 MPa), of at least 600 psig (4.14 MPa), of at least 700 psig (4.83 MPa), or of at least 800 psig (5.52 MPa). In one embodiment, the partial purification includes a water based removal of $CO_2$.

Although it can be advantageous to remove $CO_2$, $H_2O$, and/or $H_2S$ from raw biogas prior to collection and/or transport, doing so has the potential to increase capital investment and/or operating costs (e.g., for the biogas producer or another party), while potentially introducing a redundant step. Nevertheless, this approach offers some unique benefits.

One advantage is that since the partial purification can yield a partially purified biogas having a non-methane content that is greater than 10%, while still being effective for its purpose (e.g., combustion), a relatively simple and/or inexpensive partial purification module or system can be used. Such systems may have a relatively low capital investment, operating costs, associated maintenance, space requirements, and/or appear more user-friendly. For example, a water scrubber system or a relatively simple membrane system (e.g., single stage and/or low permselectivity for $CO_2/CH_4$ separations) are relatively affordable for small scale use, and are particularly suitable for partial purification of raw biogas prior to transport.

Another advantage is that with some types of biogas upgrading technologies, such as simple membrane systems, there typically is a trade-off between the recovery of a component and its purity. For example, when using a simple membrane system to separate $CH_4$ and $CO_2$, high $CH_4$ yields are typically associated with a relatively large $CO_2$ content. Alternatively, if relatively pure $CH_4$ is to be recovered (e.g., with little $CO_2$), the $CH_4$ yield will be lower since some of the $CH_4$ will be lost in the off-gas with the $CO_2$. In conventional biogas upgrading, the goal is to obtain relatively pure $CH_4$, and thus a significant amount of the $CH_4$ can be lost as methane "slip". However, when providing partial purification prior to transport, the goal can be to maximize the amount of $CH_4$ transported, while removing only some of the $CO_2$. Accordingly, in this configuration, the trade-off is an advantage and/or facilitates the use of less expensive equipment.

In one embodiment, the raw or partially purified biogas is subject to a biogas upgrading. "Biogas upgrading" refers to a type of biogas purification wherein the calorific value of biogas is increased by removing at least $CO_2$ and/or $N_2$, and typically some other contaminants, thereby increasing the relative amount of $CH_4$.

In one embodiment, raw biogas is upgraded at a processing site at or close to the corresponding biogas source 60*i*, 60*ii*, 60*iii* (e.g., before transport in the mobile vessel). In one embodiment, raw biogas is upgraded to RNG at a processing site at or close to the corresponding biogas source 60*i*, 60*ii*, 60*iii* (e.g., before transport in the mobile vessel). In one embodiment, raw biogas is upgraded to at least 850 BTU/scf, at least 900 BTU/scf, or at least 925 BTU/scf at a processing site at or close to the corresponding biogas source 60*i*, 60*ii*, 60*iii* (e.g., before transport in the mobile vessel).

In one embodiment, raw biogas is upgraded after it has been transported in the one or more mobile vessels (e.g., at the fuel production facility). In one embodiment, raw biogas is upgraded to RNG after it has been transported in the one or more mobile vessels (e.g., at the fuel production facility). In one embodiment, raw biogas is upgraded to at least 850 BTU/scf, at least 900 BTU/scf, or at least 925 BTU/scf after it has been transported in the one or more mobile vessels (e.g., at the fuel production facility).

In one embodiment, the raw or partially purified biogas is upgraded using a biogas upgrading system that includes one or more units and/or stages that remove non-methane components from the biogas (e.g., $CO_2$, $N_2$, $H_2O$, $H_2S$, $O_2$, $NH_3$, VOCs, siloxanes, and/or particulates). These non-methane components may be removed by any combination of chemical and/or physical technologies, in one or more stages. For example, one stage may remove more than one non-methane component. The removal of $H_2O$, $H_2S$, $O_2$, $NH_3$, VOCs, siloxanes, and/or particulates may be referred to as biogas cleaning. In one embodiment, the biogas upgrading system includes one or more purification units known in the art for cleaning and/or upgrading biogas. For example, $H_2O$ may be removed using a standard biogas dehumidifier, whereas $H_2S$ may be removed using a commercial $H_2S$ removal unit (e.g., based on activated carbon, molecular sieve, iron sponge, water scrubbing, NaOH washing, and/or biofilter or biotrickling filter technologies). Some $H_2S$ may also be removed during the water removal step, if present. $O_2$ may be removed by catalytic oxidation, membranes, or low pressure PSA. $CO_2$ may be removed by absorption (e.g., water scrubbing, organic physical scrubbing, chemical scrubbing), pressure swing adsorption (PSA), membrane permeation, and/or cryogenic upgrading.

In one embodiment, the biogas (i.e., raw, partially purified, or RNG) is stored prior to collection and transport (e.g., at the processing site). The biogas can be stored using any suitable storage system (e.g., including any vessel). For example, the biogas can be stored in a storage system that includes permanent storage tanks and/or mobile vessels.

In one embodiment, the biogas (i.e., raw, partially purified, or RNG) is stored in one or more mobile vessels (e.g., a batch container that can contain gas and that can be moved from one location to another). For example, in one embodiment, the biogas is fed into one or more cylinders mounted to or within a trailer, skid, or shipping container that is attachable and detachable from a truck (e.g., a tractor unit). Some examples of systems that include one or more mobile vessels are tube trailers and cylinder trailers.

In one embodiment, the biogas (i.e., raw, partially purified, or RNG) is fed into one or more mobile vessels as it is produced (e.g., as partially purified biogas is produced, it is fed to the one or more mobile vessels where it accumulates). The one or more mobile vessels may be arranged to fill in tandem or parallel. For example, in one embodiment, the biogas is fed to a single trailer until the trailer is at capacity before the biogas is fed to another trailer. In one embodiment, biogas is simultaneously fed to a plurality of trailers. Feeding the biogas to a plurality of trailers is advantageous in that the fill rate may be lower. A lower fill rate may allow more time for the heat generated from the compression to dissipate and/or may increase the duration between collection times.

In many instances, raw biogas is obtained at pressures less than 10 psi (e.g., 2-3 psi). Depending on the system and/or technology used for the partial purification and/or biogas upgrading, the pressure of the biogas may be at a higher pressure (e.g., about 200 psig (1.38 MPa) for a membrane separation). It can be advantageous to compress the biogas (i.e., raw, partially purified, or RNG) to pressures above 1500 psig (10.34 MPa), or above 2000 psig (13.79 MPa), for storage in a mobile vessel, as many trailers are designed to transport high-pressure gas (e.g., about 2000-3600 psig), and thus this increases the amount of methane per vessel. In one embodiment, the partially purified biogas is compressed to at least 1000 psig (6.89 MPa), to at least 1500 psig (10.34 MPa), or to at least 2000 psig (13.79 MPa). In one embodiment, the biogas is compressed to between 2000 psig (13.79 MPa) and 4500 psig (31.03 MPa). In one embodiment, the biogas is compressed to between 2400 psig (16.55 MPa) and 4000 psig (27.58 MPa). In one embodiment, the biogas is compressed to between 2800 psig (19.30 MPa) and 4200 psig (28.96 MPa). In one embodiment, the biogas is compressed to between 3400 psig (23.44 MPa) and 3600 psig (24.82 MPa). In one embodiment, the biogas is compressed to about 3500 psig (24.13 MPa). In one embodiment, the biogas is compressed to about 3000 psig (20.68 MPa).

Filling one or more mobile vessels with compressed biogas as the biogas is produced is advantageous in that it may obviate the need for buffer storage, may obviate transferring the biogas gas between storage vessels (e.g., which may involve compression and/or decompression), and will generally be more efficient in terms of collecting the biogas for transport. For example, once a mobile vessel is at the desired fill level (e.g., at capacity), the entire vessel can be collected (e.g., picked-up) and/or transported.

In one embodiment each mobile vessel is integrated with a truck. In one embodiment, each mobile vessel is mounted to or mounted within a skid, trailer or shipping container, where the skid, trailer or shipping container can be loaded directly onto or otherwise coupled to the mode of transportation (e.g., a vehicle such as a truck, ship, rail car) for transport. For example, a tube trailer can be temporarily parked at the processing site until it is filled and/or collection is arranged, at which point it is detachably coupled to the truck tractor, and transported.

In one embodiment, compressed biogas is fed into one or more trailers (i.e., having a mobile vessel) that are temporarily parked at the processing site. Once the trailers are filled to the desired level, which may for example take between 1.5 and 3 hours, they may be coupled to a truck (e.g., the same truck or different trucks) and transported.

In one embodiment, compressed biogas is fed into one or more trucks (i.e., having a mobile vessel) that are temporarily parked at the processing site. Once the trucks are filled substantially to full capacity or otherwise to the desired level, which may, for example, take several hours (e.g., about 1.5 to about 3 hours), they may be transported directly to the receiving station. Optionally, the mobile storage vessels are removably connected to the trucks.

Transporting the Biogas

In general, the one or more mobile vessels containing biogas (i.e., raw, partially purified, or RNG) may be collected (e.g., picked-up) and/or transported using any suitable vehicle. In one embodiment, the collection of the biogas includes transporting the one or more mobile vessels containing biogas at least some distance by truck, rail, or ship (e.g., at least 1 mile). In one embodiment, the biogas is transported by vehicle a distance that is between 1 mile and 200 miles, between 2 miles and 150 miles, or between 3 miles and 100 miles. In one embodiment, the transport includes a combination of transporting the biogas in a mobile vessel and transporting the biogas via pipeline. The term "pipeline", as used herein, refers to a single pipe or an interconnected network of pipes (e.g., physically connected), including any associated pumps and valves.

In one embodiment, where the biogas (i.e., raw, partially purified, or RNG) is fed into one or more mobile vessels prior to transport, once the mobile vessels have reached a certain fill level (e.g., based on pressure or density), or a pick-up is arranged, the mobile vessels are transported via a truck, rail, and/or ship. For example, in one embodiment, the one or more mobile vessels are mounted in/to a shipping container that can be loaded onto a truck bed or trailer bed for transport. In one embodiment, each mobile vessel is mounted to a trailer that can be coupled to a truck (e.g., a towing truck, a tractor unit, a leading trailer, or some prime moving vehicle) for transport.

In one embodiment, a trailer including one or more mobile vessels containing high pressure biogas (e.g., 3000 psi) is collected from the processing site and is then transported to a receiving station where the biogas is unloaded (e.g., at a facility at which the biofuel is produced). A trailer containing one or more empty vessels (e.g., under 200 psi) is then transported back to the processing site, or another processing site, for exchange with a trailer containing one or more mobile vessels containing high pressure biogas.

In one embodiment, a single truck is provided to transport vessels containing biogas (i.e., raw, partially purified, or RNG) directly to the receiving station (e.g., direct route). In one embodiment, a plurality of trucks is provided to transport mobile vessels containing biogas directly to the receiving station (e.g., direct route). In one embodiment, the trucks are fueled by biogas, bio-CNG, or bio-LNG. In general, the number of mobile vessels (e.g., trailers) temporarily associated with a processing site will depend on the production rate of raw biogas and/or the distance of the processing site from the receiving station.

Collecting or arranging for the collection of biogas from one or more processing sites advantageously can exploit the use of stationary purification/upgrading units and mobile vessels. Accordingly, the process/system is more efficient. For example, when partially purified biogas is produced by a stationary partial purification unit, collection (e.g., pick-up) of the partially purified biogas can be more expedient as most or all of the partially purified biogas can be produced, compressed, and/or stored before the pick-up.

Once transported, the biogas (i.e., raw, partially purified, or RNG) can be depressurized and removed from the mobile vessel(s). For example, in one embodiment, the one or more mobile vessels are transported to a receiving station that includes a pressure let down unit provided on a manifold that receives the pressurized biogas from different mobile vessels. Advantageously, transporting the biogas in mobile vessels may obviate the need for dedicated buffer storage at or near the receiving station. For example, since the biogas is transported in mobile vessels, the biogas can be stored therein until required. Moreover, since the biogas may be transported at high pressure, this higher pressure may be exploited during the production process.

In some cases, challenges may arise when the biogas contains a significant amount of $CO_2$ and/or is stored at high pressure. For example, there may be issues with freezing of the lines as $CO_2$ gas could form dry ice upon depressurization. In one embodiment, problems associated with $CO_2$ freezing are minimized or avoided by using the heat generated during compression for filling the mobile vessels to maintain the biogas at an increased temperature so that, upon expansion, it does not freeze. Advantageously, this also reduces the amount of energy required to cool the gas after it is compressed. In another embodiment, problems associated with $CO_2$ freezing are addressed by heating the compressed gas before it is depressurized (e.g., at the receiving end). Advantageously, this allows more biogas to be stored. In another embodiment, problems associated with $CO_2$ freezing are addressed by displacing the biogas by feeding an alternate fluid into the vessels that has less propensity to freeze. In one embodiment, this fluid is a cleaner gas (e.g., relatively pure methane). In one embodiment, the fluid is a liquid, which pushes the biogas out to another location. In one embodiment, the biogas is displaced using a positive displacement process (e.g., a piston type of mechanism).

Producing Heat and/or Power

In general, the biogas (i.e., raw, partially purified, or RNG) transported to the receiving station will be combusted to produce heat (e.g., steam) and/or power (e.g., electricity) used in the process. The biogas may be combusted using any suitable combustion system.

In one embodiment, the biogas is raw or partially purified biogas, and the combustion system comprises a medium-BTU combustion system (e.g., configured to combust biogas having a heating value between 400-650 BTU/cf). For example, in one embodiment, the combustion system includes a medium-BTU boiler, engine, and/or gas turbine. In one embodiment, the biogas is optionally co-combusted with natural gas.

In one embodiment, the biogas is partially purified biogas or RNG, and the combustion unit comprises a boiler, engine, and/or gas turbine configured to combust natural gas or RNG (e.g., having a heating value of at least 950 BTU/scf). In one embodiment, the partially purified biogas may have a heating value of at least 650 BTU/scf, at least 700 BTU/scf, at least 750 BTU/scf, at least 800 BTU/scf, at least 850 BTU/scf, at least 900 BTU/scf, at least 925 BTU/scf, or at least 950 BTU/scf.

In one embodiment, the raw, partially purified biogas, or RNG is combusted without further purification and/or upgrading. In one embodiment, raw or partially purified biogas is further purified and/or upgraded prior to combustion. While it is not typically necessary to upgrade the biogas to pipeline quality for a properly designed combustion device, it can be advantageous to provide some cleaning and/or upgrading (e.g., to remove $H_2S$, VOCs, and siloxanes below a predetermined limit set by the manufacturer). For example, providing some cleaning and/or upgrading may keep the emissions constant and/or known, and/or may provide more stable/consistent operation.

Examples of combustion systems that can be used to produce heat and/or power for the production process include, but are not limited to, engines (e.g., used to drive pumps or coolers such as adsorption or absorption chillers), engine-generators (generator set) used to produce electricity, boilers used to provide heat, boilers followed by a steam turbine used to produce heat and/or electricity, and/or gas turbines used to produce heat and/or electricity. In one embodiment, the combustion system includes a combined heat and power (CHP) system (e.g., also referred to as a cogeneration power plant) that uses a gas turbine to produce electricity and wherein exhaust energy from the gas turbine is used to generate steam (e.g., where the steam can be used as process heat or to generate electricity).

Advantageously, using heat and/or power generated from combusting the biogas can displace fossil fuels (e.g., replace the use of heat and/or power produced from fossil sources), thereby reducing the lifecycle GHG emissions of the biofuel (i.e., relative to an analogous case where no displacement occurs). For example, combusting the biogas to produce electricity can displace natural gas used to generate on-site electricity or natural gas or coal used to generate electricity for the grid, whereas combusting the biogas to produce heat can displace natural gas used to generate on-site heat or natural gas and/or coal used to produce electricity for generating on-site heat.

Producing the Biofuel

In general, the biofuel may be any suitable fuel produced using biomass as a feedstock. The term "biomass", as used herein, refers to non-fossilized and biodegradable organic material originating from plants, animals, or micro-organisms.

In one embodiment, the feedstock is any suitable organic material or combination of organic materials. The term "organic material", as used herein, refers to a material comprising carbon from one or more biologic sources that is not obtained from underground geologic formations. In one embodiment, the feedstock is any suitable plant derived organic material comprising polysaccharides, where the polysaccharides include starch, cellulose, hemicellulose, or a combination thereof.

In one embodiment, the feedstock is an organic material, or combination of organic materials, obtained and/or derived from plants that can be treated to provide one or more sugars. The term "sugar", as used herein, includes oligosaccharides, disaccharides, monosaccharides, and/or mixtures thereof. Examples of feedstocks that can be used to produce sugars include, but are not limited to, corn, wheat, rye, sorghum, rice, potato, cassava, sugar beet, sugar cane, barley, cellulosic materials, lignocellulosic materials, or mixtures thereof. Examples of sugars that may be produced by treating such feedstocks include, but are not limited to, sucrose, glucose, and/or xylose.

In one embodiment, the feedstock is and/or comprises corn, wheat, rye, sorghum, rice, potato, cassava, sugar beet, sugar cane, and/or barley. In one embodiment, the feedstock is and/or comprises corn grain.

In one embodiment, the feedstock is and/or comprises a cellulosic and/or lignocellulosic material. In one embodiment, the feedstock is and/or comprises: (i) an energy crop; (ii) residues, byproducts or waste from the processing of plant material in a facility, or feedstock derived therefrom; (iii) agricultural residues; (iv) forestry material; (v) material derived from pulp and paper processing; and/or (vi) pulp and paper residues; and/or (vii) municipal waste or components removed or derived from municipal waste. Energy crops include biomass crops such as grasses, including C4 grasses, such as switch grass, energy cane, sorghum, cord grass, rye grass, miscanthus, reed canary grass, C3 grasses such as *Arundo donax* or a combination thereof. Residues, byproducts or waste from the processing of plant material in a facility or feedstock derived therefrom include residues remaining after obtaining sugar from plant biomass such as sugar cane bagasse, sugar cane tops and/or leaves, beet pulp, or residues remaining after removing sugar from Jerusalem artichoke or residues remaining after grain processing, such as corn fiber, corn stover or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls or corn cobs. Forestry material includes any species of hardwood or softwood. The term includes residues, byproducts, waste or non-waste material from processing any hardwood or softwood species. Examples of waste include residues from sawmills, trimmings or slash from logging operations. Pulp and paper residue, includes non-pulp and non-paper products from chemical pulping or paper making such as black liquor, spent sulfite liquor, sludge, broke, fines or precipitated lignin.

In one embodiment, the biofuel is produced using a process wherein the feedstock is treated to produce one or more sugars using any suitable process. In many cases, the treatment may depend on the feedstock and/or biofuel. For example, feedstocks such as sugar cane may be treated to release sugars by pressing the feedstock, whereas cellulosic and/or lignocellulosic feedstocks may require mechanical size reduction, chemical addition, heat treatment, and/or an enzymatic hydrolysis in order to release the sugars.

In one embodiment, the biofuel is produced using a process wherein the feedstock is treated to produce one or more sugars, and the sugars are fermented to produce the biofuel. Examples of biofuels that can be produced by fermentation of sugars (e.g., glucose, sucrose, etc.) include, but are not limited to, alcohols (e.g., ethanol, butanol, etc.).

Figure 7:
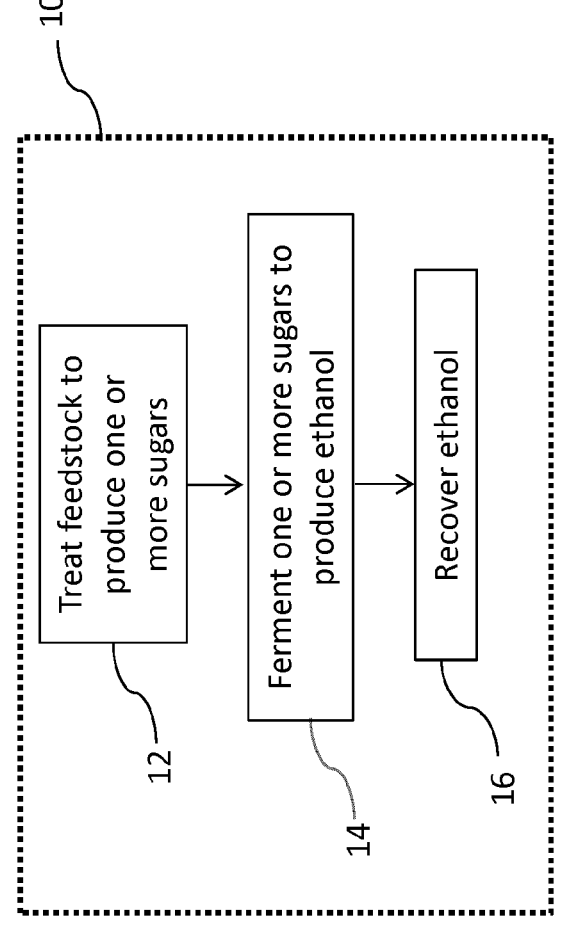
FIG. 7 is a schematic diagram showing one embodiment of a fuel production process, wherein the biofuel produced is ethanol.

Referring to FIG. 7, in one embodiment, the fuel production process 10 includes treating a feedstock to product one or more sugars 12, fermenting one or more sugars to produce ethanol 14, and recovering the ethanol 16. In one embodiment, the feedstock is corn grain and the treating includes a wet or dry milling process. In one embodiment, the feedstock is a lignocellulosic feedstock and the treating includes an acid catalyzed steam pretreatment followed by an enzymatic hydrolysis. In one embodiment, the fermenting includes adding a fermentation microorganism selected from yeast, fungi and bacteria. In one embodiment, the fermenting includes adding yeast (e.g., *Saccharomyces* spp. yeast) and fermenting at a temperature between about 25° C. and about 35° C. In one embodiment, recovering the alcohol includes a distillation (e.g., using one or more distillation columns). In one embodiment, recovering the alcohol includes a distillation and an azeotropic breaking process. In one embodiment, the distillation includes a multicolumn distillation with rectification. In one embodiment, recovering the alcohol includes a distillation and a dehydration (e.g., using a molecular sieve system), which for example, may produce 200 proof ethanol.

In one embodiment, the biofuel is produced using a process wherein the feedstock is subjected to a combustion, gasification, pyrolysis, and/or reforming in order to produce a gas (e.g., syngas) and/or liquid (e.g., oil) that is converted to the biofuel. For example, syngas may be used to produce hydrogen or a liquid fuel (e.g., transportation fuel). Syngas may be produced, for example, by gasifying a solid material (e.g., lignin pellets, woodchips, etc.), or reforming a methane containing gas (e.g., upgraded landfill gas).

In one embodiment, the biofuel is a liquid biofuel. In one embodiment, the biofuel is a liquid transportation fuel. In one embodiment, the biofuel is a transportation fuel. In one embodiment, the biofuel is an alcohol. In one embodiment, the feedstock is corn grain, and the biofuel is ethanol. In one embodiment, the feedstock is a lignocellulosic feedstock, and the biofuel is ethanol.

In one embodiment, the feedstock is biomass used to produce biogas, and the fuel production process includes converting the biogas to a biofuel other than RNG, bio-RNG, or bio-LNG, in one or more processing steps. In one embodiment, the feedstock is an organic material used to produce biogas, and the fuel production process includes converting the biogas to RNG, bio-RNG, or bio-LNG, in one or more processing steps.

In one embodiment, the production process produces a biofuel from biogas using a one-step conversion process (e.g., partial oxidation of methane to methanol). In one embodiment, the production process produces a biofuel from biogas using a multiple-step conversion process based on a syngas intermediate.

In one embodiment, the production process produces a biofuel from biogas and/or biomass based on a syngas intermediate. Syngas, which is a mixture including CO, $H_2$, and/or $CO_2$, may be formed by gasifying biomass (e.g., woodchips) or by subjecting a methane containing gas to methane reforming (e.g., steam methane reforming (SMR), autothermal reforming (ATR), dry methane reforming (DMR), or partial oxidation (POX)). In one embodiment, the fuel production process produces syngas using a methane reforming reaction and a water gas shift (WGS) reaction.

In embodiments wherein the fuel production process produces a biofuel from biogas, this biogas feedstock may be obtained from the one or more mobile vessels and/or may be any biogas-derived methane (e.g., obtained from a commercial natural gas pipeline as RNG). The terms "biogas-derived methane" and "methane derived from biogas", as used herein, refers to methane obtained from biogas and/or to methane withdrawn from a fungible distribution system into which methane obtained from biogas is injected, where the withdrawn methane is recognized as possessing the environmental attributes of the injected methane.

In one embodiment, the fuel production process produces $H_2$. In one embodiment, $H_2$ is produced by subjecting biogas-derived methane to an SMR reaction to produce syngas, which is subject to a water gas shift reaction (WGS) to increase the concentration of the $H_2$, followed by a hydrogen purification (e.g., pressure swing adsorption (PSA) or membrane) to purify the $H_2$. In one embodiment, the purified $H_2$ is used directly as a fuel (e.g., a transportation fuel). In one embodiment, the purified $H_2$, which may be referred to as renewable $H_2$, is incorporated into a crude-oil derived liquid hydrocarbon to produce gasoline and/or diesel having renewable content (e.g., see U.S. Pat. Nos. 8,658, 026, 8,753,854, 8,945,373, 9,040,271, 10,093,540). In this embodiment, the biogas removed from the one or more mobile vessels, or a gas derived therefrom, may be combusted to produce heat and/or power for the process. For example, the heat and/or power may be used to produce the syngas (e.g., fuel the SMR), to operate compressors, etc.

In one embodiment, the fuel production process produces methanol. Methanol may be formed in a methane-to-methanol process. For example, in one embodiment, the fuel production process produces methanol from biogas-derived methane using Imperial Chemical Industries (ICI) low pressure methanol (LPM) process, Katalco low pressure methanol process, Lurgi low pressure methanol process, Haldor-Topsoe process, or liquid process such as the liquid-phase methanol synthesis process (LPMeOH). Suitable catalysts may include copper, zinc, oxide, alumina, chromium oxide, or combinations thereof. Methanol may be used as a fuel (e.g., marine fuel), may be blended with gasoline, may be used in a methanol-to-olefins process, may be used to produce dimethyl ether (DME), may be used to produce methyl tertiary butyl ether (MTBE), may be used to produce biodiesel, or may be used in a methanol-to-gasoline (MTG) process. In one embodiment, the production process produces DME, MTBE, biodiesel, or gasoline from biogas-derived methanol. In these embodiments, the biogas removed from the one or more mobile vessels, or a gas derived therefrom, may be combusted to produce heat and/or power for the process. For example, the heat and/or power may be used to produce the syngas (e.g., gasify biomass), to operate compressors, in the catalytic reactions, etc.

In one embodiment, the production process produces ethanol. Ethanol may be formed by gas fermentation of syngas with anaerobic microorganisms. Ethanol may be used as a fuel or may be blended with gasoline. In one embodiment, the production process produces ethanol by the gas fermentation of syngas produced by methane reforming of biogas-derived methane. The production of ethanol by the gas fermentation of syngas with anaerobic microorganisms is well known (e.g., see U.S. Pat. No. 10,202,622). In this embodiment, the biogas removed from the one or more mobile vessels, or a gas derived therefrom, may be combusted to produce heat and/or power for the process. For example, the heat and/or power may be used to produce the syngas, to operate compressors, distill the ethanol, etc.

In one embodiment, the production process produces gasoline. Gasoline may be produced by converting syngas to methanol, which is transformed into gasoline (e.g., a methanol-to-gasoline (MTG) process). In one embodiment, the biofuel is renewable gasoline. In this embodiment, the biogas removed from the one or more mobile vessels, or a gas derived therefrom, may be combusted to produce heat and/or power for the process. For example, the heat and/or power may be used to produce the syngas, to operate compressors, in the catalytic process, etc.

In one embodiment, the production process produces diesel. Diesel may be produced using a gas-to-liquid (GTL) refinery process where methane is converted to longer-chain hydrocarbons via a syngas intermediate. For example, diesel may be produced using a Fischer-Tropsch type process. Alternatively, diesel may be produced by incorporating renewable hydrogen into a crude-oil derived liquid hydrocarbon, where the resulting diesel has renewable content. In one embodiment, the biofuel is renewable gasoline. In these embodiments, the biogas removed from the one or more mobile vessels, or a gas derived therefrom, may be combusted to produce heat and/or power for the process. For example, the heat and/or power may be used to produce the syngas, to operate compressors, in fractional distillation, etc.

In one embodiment, the production process produces DME. DME may be produced by catalytic dehydration of methanol. DME may be used as a fuel for diesel engines (e.g., a clean diesel alternative). In one embodiment, the biofuel is DME. In one embodiment, the biofuel is renewable gasoline. In this embodiment, the biogas removed from the one or more mobile vessels, or a gas derived therefrom, may be combusted to produce heat and/or power for the process. For example, the heat and/or power may be used to produce the syngas, to operate compressors, in the catalytic process, etc.

In the above embodiments where the biofuel is derived from biogas, the feedstock may be obtained from the one or more mobile vessels or may be any biogas-derived methane. In one embodiment, the biogas from the one or more mobile vessels is used primarily for producing heat and/or power for the fuel production process, while methane obtained from a commercial natural gas pipeline as RNG is converted to the biofuel. This embodiment is particularly advantageous as RNG purchased from the pipeline cannot be used to reduce the CI of a biofuel under some regulations, but is recognized as a renewable source of carbon for conversion to a biofuel. Further advantageously, since many processes that can convert methane to a biofuel can require significant utilities (e.g., electricity and/or natural gas), this embodiment may provide a biofuel with significantly reduced carbon intensity.

Reducing GHG Emissions

In general, the heat and/or power generated by combusting the biogas (i.e., raw, partially purified, and/or RNG) may be used in the production process, and thus, may reduce lifecycle GHG emissions and/or a carbon intensity (CI) of the biofuel.

In one embodiment, heat and/or power generated by combusting the biogas (i.e., raw, partially purified, and/or RNG) is used to in the production process such that it displaces fossil fuels (e.g., natural gas, coal, etc.) that otherwise would have been used to produce the heat and/or power required for the process. For example, combusting the biogas to produce electricity can displace natural gas used to generate on-site electricity and/or natural gas or coal used to generate electricity for the grid, whereas combusting the biogas to produce heat can displace natural gas used to generate on-site heat and/or natural gas or coal used to produce electricity for generating on-site heat.

In one embodiment, the biogas is fed to a combustion system designed to produce heat and/or electricity (e.g., boiler and/or turbine) that can be used throughout the process. For example, thermal energy may be used for cooking, distillation, and/or drying steps, whereas electricity may be used to operate motors, fans, compressors, and/or pumps. In one embodiment, the biogas is fed to specific combustion equipment (e.g., direct fired thermal oxidizer, steam methane reformer, etc.).

In one embodiment, the biogas is combusted to produce heat, which is used in treating the feedstock. For example, in one embodiment, the process includes producing steam using the biogas. In one embodiment, the feedstock is a lignocellulosic feedstock (e.g., bagasse, corn stover, wheat straw, etc.), and the steam is used to treat the feedstock in steam pretreatment (e.g., at a temperature above 180° C.). In one embodiment, the feedstock is a woody feedstock, and the steam is used to pre-steam the feedstock prior to chemical addition. In one embodiment, the feedstock is corn grain, and the steam is used for liquefaction and/or saccharification steps.

In one embodiment, the biogas is combusted to produce heat, which is used in recovering the biofuel. For example, in one embodiment, the process includes combusting biogas to produce steam for use in distillation (e.g., in one or more distillation and/or rectification columns).

In one embodiment, the biogas is combusted to produce heat, which is used in producing a co-product. For example, in one embodiment, the process includes producing steam that is used in a dryer (e.g., rotary drum dryer) used to dry distiller's grains and/or prepare DDGS. In one embodiment, the process includes producing steam that is used in a steam dryer for drying sugar beet pulp. In one embodiment, the process includes producing steam that is used in an evaporator system used to concentrate thin stillage and produce syrup.

In one embodiment, the biogas is combusted to produce electricity, which is used throughout the production process. For example, in one embodiment, the biofuel is ethanol, and the electricity is used in treating the feedstock, providing mixing during fermentation, and/or in recovery of the ethanol and/or $CO_2$ produced during fermentation.

In one embodiment, the biogas is combusted to produce heat, which is used in the fuel production process. For example, in one embodiment, the biogas from the one or more mobile vessels is used as a fuel for a steam methane reformer, while RNG from a commercial distribution system is used as feedstock.

In one embodiment, the biogas is used for a thermal oxidizer. For example, thermal oxidizers are used as air pollution control systems for dryers used for distiller's grains which can produce emissions such as volatile organic compounds (VOCs) and/or hazardous air pollutants (HAPs). When the thermal oxidizer is positioned upstream of a heat recovery steam generator (HRSG), the biogas is also used to produce steam that may be used for the process. Accordingly, the lifecycle GHG emissions and/or CI may be further reduced.

In one embodiment, the biogas is combusted to fuel a dryer (e.g., direct or indirect). In one embodiment, the biogas is combusted in a direct fired dryer (e.g., natural gas fired rotary drum dryer). In one embodiment, the biogas is combusted to produce steam for a dryer (indirect or direct). In one embodiment, the biogas is combusted to produce steam for a rotary drum dryer (e.g., tube). In one embodiment, the biogas is combusted to generate super-heated steam used for direct drying.

In one embodiment, the biogas is combusted in a boiler to produce steam for a steam dryer used to dry distiller's grain, and some of this energy is reclaimed by using steam exiting the steam dryer within the fuel production process (e.g., in the beer column reboiler). Accordingly, the lifecycle GHG emissions and/or CI may be further reduced.

In general, the GHG emission reduction and/or change in CI, may be dependent, at least in part, on how much fossil fuel is displaced and/or the carbon intensity of the biogas. For example, consider an example where natural gas having a carbon intensity of about 80 $gCO_2e/MJ$, is displaced with biogas. The GHG emission reduction will be much larger if the biogas is produced from swine manure and has a carbon intensity of −350 $gCO_2e/MJ$ than if the biogas is landfill gas having a carbon intensity of +50 $gCO_2e/MJ$.

Typically, when the goal is to reduce the lifecycle GHG emissions and/or CI of a biofuel, the process is optimized to reduce energy use. For example, since drying distiller's grains with solubles can use a significant portion (e.g., about 30% or more) of the total energy required for the production of a liter of ethanol, one option to decrease the CI of corn ethanol is to provide wet distillers grain with solubles. However, as recognized herein, by being able to collect very low CI biogas (e.g., less than −100 $gCO_2e/MJ$) using mobile vessels, and using this biogas for the production process, the CI of the resulting ethanol can be reduced significantly (e.g., to less than 30 $gCO_2e/MJ$, less than 20 $gCO_2e/MJ$, less than 10 $gCO_2e/MJ$, or less than 5 $gCO_2e/MJ$), even when the process produces DDGS. In some cases, fuel ethanol having a CI of about zero may be obtained. Advantageously, in these cases, the CI can be reduced more (i.e., in g/MJ) for ethanol produced with DDGS than for ethanol produced with WDGS, depending on how much fossil fuel is displaced. In one embodiment, at least 10%, at least 20%, at least 30%, at least 40%, or at least 50% of the plant's fuel methane is derived from biogas.

In one embodiment, a fuel credit or renewable energy credit associated with the biogas and/or biofuel is generated or caused to be generated. The term "cause" or "causing", as used herein, refers to arranging or bringing about a specific result (e.g., a withdrawal of a gas from a distribution system), either directly or indirectly, or playing a role in a series of activities through commercial arrangements such as a written agreement, verbal agreement, or contract.

The term "credit", "renewable fuel credit", or "fuel credit", as used herein, refers to any rights, credits, revenues, offsets, greenhouse gas rights, or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. The renewable fuel credit may be a certificate, record, serial number or guarantee, in any form, including electronic, which evidences production of a quantity of fuel meeting certain life cycle GHG emission reductions relative to a baseline (e.g., a gasoline baseline) set by a government authority.

The generation of fuel credits or renewable energy credit associated with the biogas and/or biofuel may be related to the environmental attributes thereof and/or the corresponding life cycle GHG emission emissions. To determine life cycle GHG emissions associated with a fuel, analyses are conducted to calculate the GHG emissions related to the production and use of the fuel throughout its life cycle. Life cycle GHG emissions include the aggregate quantity of GHG emissions related to the full life cycle of the fuel, including all stages of fuel and feedstock production and distribution, from feedstock generation or extraction, through the distribution and delivery, and use of the finished fuel to the ultimate consumer. GHG emissions typically account for total net GHG emissions, both direct and indirect, associated with feedstock production and distribution, the fuel production, and distribution and use.

In one embodiment, the biofuel produced is a transportation fuel, and a fuel credit is generated or is caused to be generated. Fuel credits, such as Renewable Identification Numbers (RINs) under the US Environmental Protection Agency (EPA) Renewable Fuel Standard, or carbon credits under state supported low carbon fuel standards, can be lucrative.

In one embodiment, the transportation fuel and/or renewable content has life cycle GHG emissions that are at least 20% less than the life cycle GHG emissions of a gasoline baseline using EPA methodology, preferably at least 50% or 60% less.

The term "carbon intensity" or "Cr" refers to the quantity of lifecycle GHG emissions, per unit of fuel energy, and is often expressed in grams of carbon dioxide equivalent emissions per unit of fuel (e.g., $gCO_2e/MJ$ or $gCO_2e/MMBTU$). In general, the CI and/or lifecycle GHG emissions of biofuels may be calculated using any suitable method (e.g., any method recognized by the applicable regulatory authority). In one embodiment, the lifecycle GHG emissions and/or CI is evaluated using lifecycle analysis (LCA) methods. Examples of models to measure lifecycle GHG emissions associated with the production of a fermentation based fuel, such as an alcohol, include, but are not limited to:

(i) GREET Model—GHGs, Regulated Emissions, and Energy Use in Transportation, the spread-sheet analysis tool developed by Argonne National Laboratories;

(ii) FASOM Model—a partial equilibrium economic model of the U.S. forest and agricultural sectors developed by Texas A&M University;

(iii) FAPRI International Model—a worldwide agricultural sector economic model that was run by the Center for Agricultural and Rural Development ("CARD") at Iowa State University;

(iv) GTAP Model—the Global Trade Analysis Project model, a multi-region, multi-sector computable general equilibrium model that estimates changes in world agricultural production as well as multiple additional models; and (v) ISO (International Organization for Standardization) standards for GHG emissions accounting and verification—provides guidance for quantification, monitoring and reporting of activities intended to cause greenhouse gas (GHG) emission reductions or removal enhancements.

The CI values recited herein are determined using the CA-GREET model (e.g., see, https://ww2.arb.ca.gov/resources/documents/lcfs-life-cycle-analysis-models-and-documentation), unless otherwise specified.

In one embodiment, the lifecycle GHG emissions and/or CI of the biofuel is further reduced by collecting $CO_2$ removed from the biogas (e.g., at the fuel production facility or at the processing site at or close to the corresponding biogas source). The collected $CO_2$ is then used as a resource to create valuable products or services, or stored (e.g., permanently sequestered underground in geological formations such as abandoned oil and/or gas fields or deep saline formations). This carbon capture, utilization, and storage (CCUS) approach can further reduce the lifecycle GHG emissions and/or CI of the biofuel as the $CO_2$ from the biogas is biogenic, and removing the biogenic $CO_2$ from the atmosphere (or preventing its release to the atmosphere) provides the foundation for carbon removal or negative emissions. Advantageously, when the $CO_2$ is removed at a fuel production facility, from biogas from a plurality of biogas sources, the CCUS approach benefits from economies of scale and improved economics. As used herein, CCUS encompasses both carbon capture and storage (CCS) and carbon capture and utilization (CCU). For example, CCU can include the production of fuels and/or chemicals using the $CO_2$.

In one embodiment, the lifecycle GHG emissions and/or CI of the biofuel is further reduced by capturing $CO_2$ produced during the fermentation. The $CO_2$ released from ethanol production can be of relatively high purity and can be used as a resource to create valuable products or services, or can be stored (e.g., permanently sequestered underground in geological formations such as abandoned oil and/or gas fields or deep saline formations). This CCUS approach can further reduce the lifecycle GHG emissions and/or CI of the biofuel as $CO_2$ from the fermentation is biogenic.

In one embodiment, both $CO_2$ from the ethanol fermentation and $CO_2$ from the biogas is collected and used as a resource to create valuable products or services, or is stored (e.g., permanently sequestered underground in geological formations such as abandoned oil and/or gas fields or deep saline formations).

Description of Embodiments of the Invention

Figure 8:
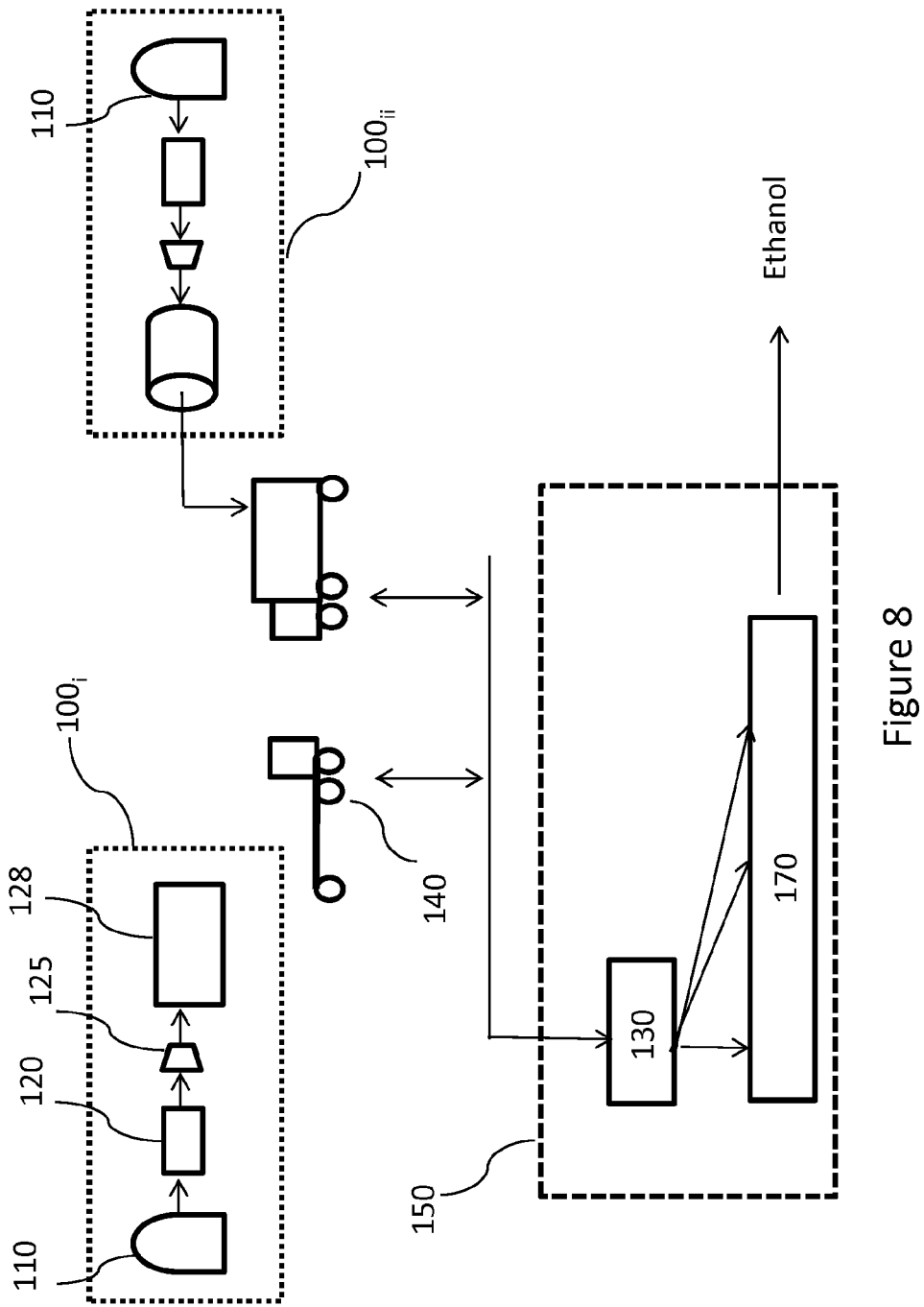
FIG. 8 is a schematic diagram showing one embodiment of a process for producing one or more biofuels.

Referring to FIG. 8, there is shown a system in accordance with one embodiment. The system includes a plurality of processing sites $100_i$ and $100_{ii}$, each of which includes a source of raw biogas 110 (e.g., one or more anaerobic digesters) and a partial purification system 120 (i.e., for removing $H_2O$, $H_2S$, and/or $CO_2$ from raw biogas), and optionally includes a compressor system 125 and/or a storage system 128 (e.g., one or more mobile vessels). The system also includes a collection system 140 (e.g., including one or more vehicles such as a truck, ship, or rail car), for collecting and transporting the partially purified biogas produced at each biogas processing site $100_i$, $100_{ii}$ to a corn ethanol plant 150. The biogas is transported in the one or more pressurized mobile vessels. The corn ethanol plant 150 includes a receiving station (not shown) for receiving the partially purified biogas and unloading the same from one or more mobile vessels.

Advantageously, since the receiving station can receive partially purified biogas from a plurality of processing sites, it may provide the partially purified biogas to the combustion system 130 on a relatively large scale and/or in a continuous fashion. In addition, since the biogas is transported in the one or more mobile vessels at relatively high pressures (e.g., at least 2000 psig (13.79 MPa)), the partially purified biogas may be fed to the combustion system 130 (e.g., gas turbine) at a relatively high pressure (e.g., greater than 100 psig (0.69 MPa), greater than 200 psig (1.38 MPa), greater than 300 psig (2.07 MPa), greater than 400 psig (2.76 MPa), greater than 500 psig (3.45 MPa), or greater than 600 psig (4.14 MPa)) without requiring significant compression. When the combustion system (e.g., a gas turbine) requires a relatively high pressure feed (e.g., greater than 150 psig), this may reduce energy requirements per unit of ethanol and/or reduce the CI of the ethanol (e.g., compared to if the same biogas was depressurized to 30 psig).

In one embodiment, the partial purification increases the heating value of the biogas by at least 100 BTU/scf (e.g., from about 600 BTU/scf to at least 900 BTU/scf). Accordingly, the cost of compressing the partially purified biogas as it fills the one or more mobile vessels may be reduced, and/or more methane may be transported per mobile vessel. Advantageously, this level of partial purification may facilitate using the partially purified biogas for the combustion system 130 without additional cleaning and/or upgrading.

Once the partially purified biogas is removed from the one or more mobile vessels and combusted, the heat and/or power generated may be used in the corn ethanol production process 170 to produce the ethanol. A traditional ethanol production process can use relatively high amounts of energy. For example, a corn ethanol plant may use as much as 30,000 BTU of natural gas and 1.0 kw*h of electricity for every gallon of ethanol produced. For an ethanol plant producing between about 140,000 and 280,000 gallons of ethanol per day, this may correspond to about 4200 to about 8400 MMBtu of natural gas per day. The natural gas may be used primarily for heating and drying, whereas the electricity may supply other operational power needs.

In one embodiment, the corn ethanol production process includes a dry milling process, wherein the corn grain is milled to flour and used to produce a slurry. The slurry is treated with one or more enzymes to convert the starch in the slurry to sugar (e.g., glucose), thereby creating a slurry mash. A fermentation organism, such as yeast, is added to the mash, to convert the sugar to beer. The ethanol in this beer is removed using one or more distillation columns, thereby producing whole stillage. The whole stillage is separated into wet cake and thin stillage (e.g., using a decanting centrifuge). Some of the thin stillage may be recycled upstream as make-up water for slurrying fresh grain. The remaining thin stillage may be sent to a multi-effect evaporator to produce syrup. Evaporator overheads may be condensed to evaporator condensate, which may also be used as make-up water. Grain oil may be recovered from the concentrated thin stillage. Syrup from the last stage of evaporation may be sold as is or added to wet cake and sold as either WDGS, or more commonly, DDGS. DDGS may be produced by drying the wet cake and syrup in an industrial dryer (e.g., a rotatory dryer and/or steam tube dryer).

The heat and/or power generated from the partially purified biogas can be used in the milling, fermentation, distillation, and/or DDGS production. For example, in one embodiment, the biogas is used to fuel a dryer used to dry the wet cake to produce relatively drier solids (e.g., DDGS).

Figure 9:
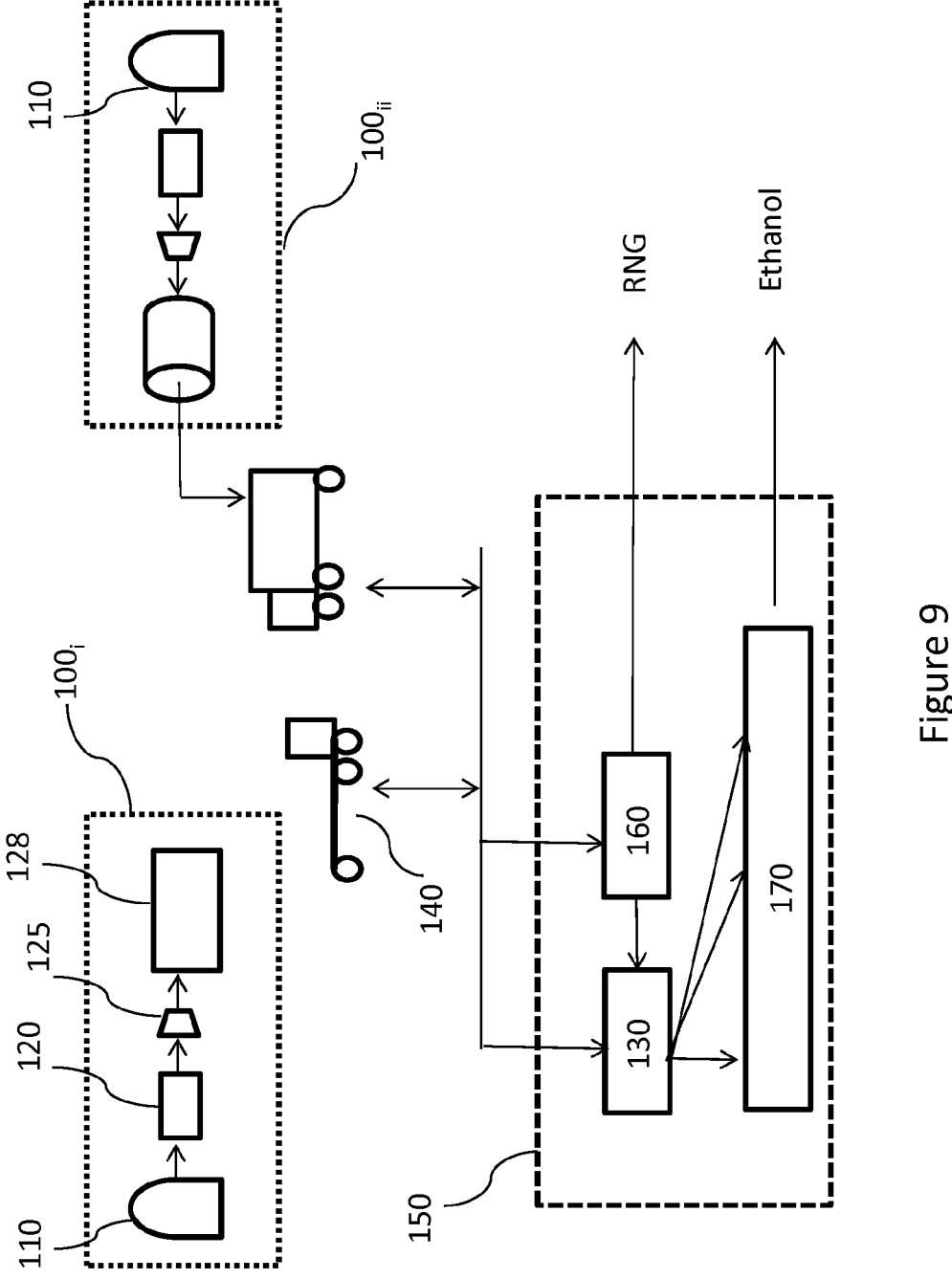
FIG. 9 is a schematic diagram showing another embodiment of a process for producing one or more biofuels.

In the embodiment illustrated in FIG. 9, the biogas removed from the one or more mobile vessels is fed directly to one or more combustion units 130 or to a biogas upgrading system 160, in dependence upon its non-methane content and the system requirements of the combustion system. For example, if the partial purification system 120 includes a membrane that removes most of the $CO_2$, then the partially purified biogas may fed directly into the combustion unit 130, whereas if the biogas is raw biogas or cleaned biogas, it may be fed to the biogas upgrading system 160 (which may or may not produce RNG quality gas). Any excess biogas not used to provide heat and/or power for the process 170 may be injected into commercial distribution system (e.g., as RNG) or used as feedstock in the process (if applicable).

Advantageously, the systems illustrated in FIGS. 8 and 9 may provide a relatively large and/or constant supply of partially purified biogas for the fuel production facility 150. For example, if the biogas is partially purified to provide a gas having a heating value of about 900 Btu/scf, and is used to fill a mobile vessel that can contain about 350,000 scf (e.g., at a pressure above about 3600 psig (24.82 MPa)), then each delivery may provide about 320 MMBtu. Accordingly, about 2000 MMBtu/day may be provided by about 6 or 7 mobile vessels. Preliminary calculations have indicated that if biogas having a CI of −350 gCO₂e/MJ is provided at a rate of about 3400 MMBtu/day is used in a corn ethanol plant producing DDGS and using about 7900 MMBtu/day of natural gas, that the corn ethanol could have a CI close to zero.

In accordance with one embodiment, the depressurization of the one or more mobile vessels is used to reduce the natural gas and/or electricity utilities (e.g., per day or per unit of biofuel) and/or reduce net energy requirements per unit of biofuel (e.g., relative to the same process where the compressed state of the partially purified biogas is not utilized). For example, since the receiving station may receive multiple mobile vessels throughout the day, the depressurization of these vessels may be used to produce cooling, electricity, or increased pressure that can be used in the process. In one embodiment, as the partially purified biogas is unloaded from each mobile vessel, it is depressurized such that it is significantly cooled (e.g., to 10° C., 0° C., −10° C., −20° C., −30° C., −40° C., −50° C., −60° C., −70° C., or −80° C.). This relatively cold partially purified biogas is passed through a heat exchanger, where it is warmed, and the cooled heat transfer medium is then used to provide cooling in the process (e.g., for the condensers in the distillation system, condensers in the evaporator, and/or for cooling DDGS downstream of the drying). Accordingly, the instant system can prevent bottlenecks associated with limitations in cooling capacity within corn ethanol plants (e.g., in the summer), thereby increasing yields.

Figure 10:
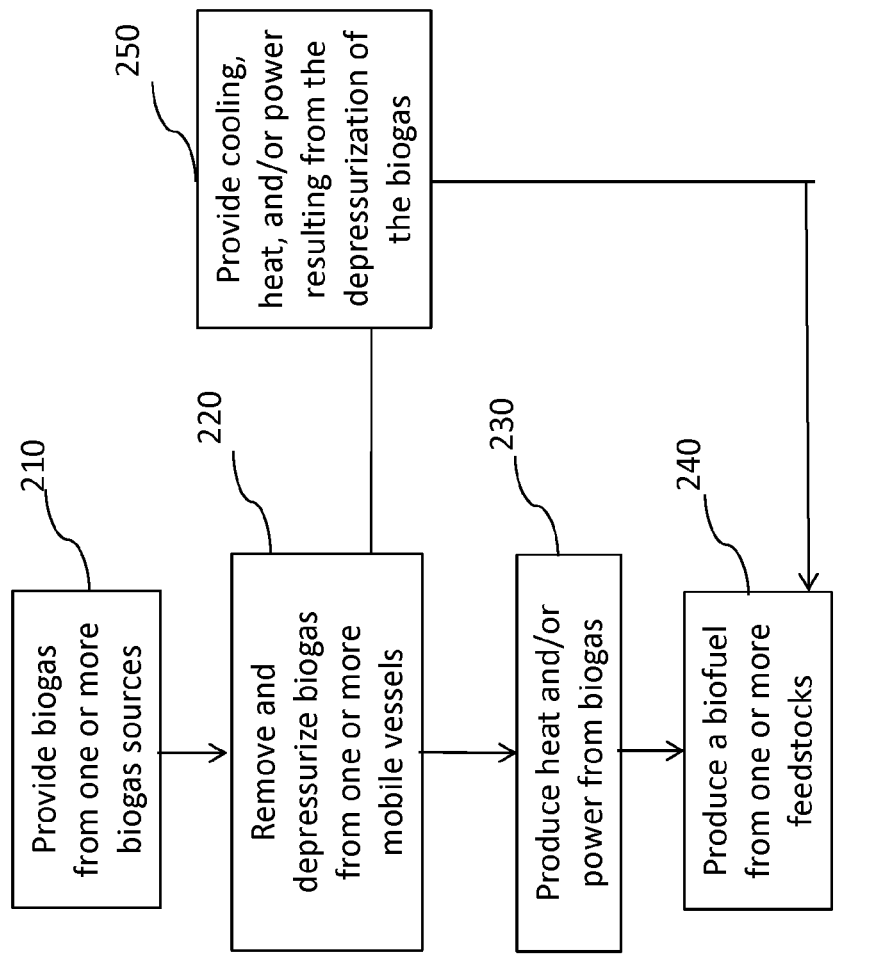
FIG. 10 is a flow diagram showing one embodiment of a process for producing one or more biofuels.

Referring to FIG. 10, there is shown a process for producing one or more biofuels in accordance with one embodiment. The process includes providing biogas from one or more biogas sources 210, where the biogas is provided in one or more mobile vessels. For example, in one embodiment, each mobile vessel contains biogas from one biogas source (e.g., a manure digester) that is transported by vehicle to a facility for producing the biofuel. In one embodiment, each mobile vessel is pressurized to at least 1000 psig (6.89 MPa), at least 1500 psig (10.34 MPa), at least 2000 psig (13.79 MPa), or at least 2900 psig (19.99 MPa). The biogas in each mobile vessel may be raw biogas, partially purified biogas, or RNG (e.g., may have been subject to a partial purification or biogas upgrading before being compressed and fed into the respective mobile vessel). Once transported to the fuel production facility, the biogas in each mobile vessel is removed and depressurized 220 and fed to one or more combustion units that provide heat and/or power 230 for producing the biofuel 240. In one embodiment, at least 10% the methane used to produce a unit of the biofuel is derived from the biogas. In one embodiment, at least 20%, 30%, 40%, 50%, or 60% the methane used to produce a unit of the biofuel is derived from the biogas. In one embodiment, the biogas has a CI that does not exceed 0 gCO₂e/MJ, −100 gCO₂e/MJ, −200 gCO₂e/MJ, or −300 gCO₂e/MJ (i.e., has a negative value).

The combination of using a relatively low CI biogas and displacing a significant amount of fossil fuel used to produce the biofuel, can significantly reduce the lifecycle GHG emissions and/or CI of the biofuel. In one embodiment, a quantity of biogas used to produce the heat and/or power, and to displace fossil fuel is sufficient to reduce a carbon intensity of the biofuel by at least 5 gCO₂e/MJ, at least 10 gCO₂e/MJ, at least 15 gCO₂e/MJ, at least 20 gCO₂e/MJ, or at least at least 25 gCO₂e/MJ (i.e., relative to an analogous case where there is no displacement).

Although, compressing and transporting the biogas at relatively high pressures can contribute to the GHG emissions of the process, in this embodiment, the process includes using a depressurization method that can reduce the process energy requirements per unit of biofuel.

In one embodiment, the biogas is obtained from dairy or swine digesters, each of which is within at least 100, 150, 200, or at least 300 miles from the fuel production facility, and which is provided for a relatively large herd.

In one embodiment, the biogas is used to provide at least 500 MMBtu/day, at least 750 MMBtu/day, at least 1000 MMBtu/day, at least 1400 MMBtu/day, at least 1800 MMBtu/day, at least 2200 MMBtu/day, at least 2600 MMBtu/day, at least 3000 MMBtu/day, at least 3400 MMBtu/day, or at least 3800 MMBtu/day of biogas.

In one embodiment, at least at least 2,500 BTU, at least 5,000 BTU, at least 7,000 BTU, at least 8,000 BTU, at least 9,000 BTU, at least 10,000 BTU, at least 11,000 BTU, at least at least 12,000 BTU, at least 13,000 BTU, at least 14,000 BTU, or at least at least 15,000 BTU of biogas is provided per gallon of ethanol produced.

Advantageously, the above-described embodiments may facilitate the production of corn ethanol wherein the CI is lower than the CI contribution from the land use change and agricultural practices (e.g., including the production of fertilizer and soil amendments). In one embodiment, sufficient biogas is provided to reduce CI of the biofuel below a CI value that corresponds to the sum of the CI contribution from the land use change and the CI contribution from agricultural practices.

Further advantageously, the above-described embodiments may be used to produce any suitable biofuel or biofuel intermediate. For example, while the above embodiments are discussed with reference to producing a biofuel (e.g., ethanol), which for example may be used as a transportation fuel, they also apply to producing biofuel intermediates (e.g., methanol) that are eventually converted to a biofuel. In one embodiment, the biogas is used to provide at least 20%, at least 30%, at least 40%, or at least 50% of the production plant's natural gas needs.

In one embodiment, there is provided a method of reducing a carbon intensity of a biofuel produced in a process comprising treating a feedstock to release one or more sugars (e.g., by pressing, treatment with heat, treatment with acid, and/or treatment with enzymes), subjecting the one or more sugars to a fermentation to produce a fermentation product (e.g., an alcohol such as ethanol or butanol), and recovering the fermentation product (e.g., by distillation), wherein the method includes generating heat and/or power from biogas transported to the fuel production facility in one or more mobile vessels, each mobile vessel transported at a pressure above about 1000 psig (6.89 MPa), above about 1500 psig (10.34 MPa), or above about 2000 psig (13.79 MPa), wherein the biogas is transported from one or more biogas sources (e.g., including one or more livestock farms), and wherein at least a portion of the heat and/or power is used in the process for producing the fuel.

In some embodiments, the pressurization of the biogas is used to provide work for the process for producing the fuel. For example, in one embodiment, the pressurized biogas is fed through a turboexpander. In one embodiment, the turboexpander is configured to drive a generator. In one embodiment, the turboexpander is configured to drive a shaft coupled to a compressor. Advantageously, these embodiments can further reduce the carbon intensity of the biofuel and/or provide energy savings.

In some embodiments, the pressurization of the biogas is used provide cooling for the process for producing the fuel. For example, in one embodiment, the change in pressure provided by depressurizing the biogas is used to provide cooling for pretreated feedstock, for enzymatic hydrolysis, for fermentation, for ethanol recovery, and/or for hot distiller's dried grains. Advantageously, this can further reduce the carbon intensity of the biofuel and/or can prevent and/or reduce bottlenecks in the process arising from limitations in cooling capacity (e.g., due to high heat and/or humidity in the summer). Providing cooling for ethanol recovery (e.g., distillation and/or dehydration) is particularly advantageous, and may prevent bottlenecks associated with the same.

In some embodiments, the pressurization of the biogas is used reduce the need for compression for downstream processing (e.g., for biogas upgrading and/or fuel production).

For example, in one embodiment, once removed from the one or more mobile vessels, the biogas is provided at pressures greater than about 200 psig (1.38 MPa), greater than about 400 psig (2.76 MPa), greater than about 600 psig (4.14 MPa), or greater than about 800 psig (5.52 MPa) for further processing (predominately without requiring compression). Advantageously, this can further reduce the carbon intensity of the biofuel and/or can permit the use of systems generally operated at pressures above some value (e.g., above about 200 psig (1.38 MPa), above about 400 psig (2.76 MPa), above about 600 psig (4.14 MPa), or above about 800 psig (5.52 MPa)).

In some embodiments, the one or more biogas sources comprises a plurality of biogas sources, and the method includes providing a biogas delivery system that includes a receiving station configured to simultaneously connect to a plurality of mobile vessels. In some embodiments, the biogas delivery system provides mobile vessels containing biogas from the one or more biogas sources with a frequency selected such that biogas for the production process is continuously being removed from one of the mobile vessels. In some embodiments, sufficient biogas is provided to avoid using natural gas to produce heat and/or power for the process. In some embodiments, the biogas delivery system includes one or more vehicles. In some embodiments, the one or more vehicles are trucks fueled by biogas.

In some embodiments, the biogas has a carbon intensity that does not exceed −200 $gCO_2e/MJ$ and is produced from manure. In some embodiments, the biogas has a carbon intensity that does not exceed −300 $gCO_2e/MJ$ and is produced from manure. In some embodiments, the biofuel is ethanol, and the amount of biogas used in the process is sufficient to provide the ethanol with a carbon intensity that does not exceed 30 $gCO_2e/MJ$. In some embodiments, the biofuel is ethanol, and the amount of biogas used in the process is sufficient to provide the ethanol with a carbon intensity that does not exceed 20 $gCO_2e/MJ$. In some embodiments, the biofuel is ethanol, and the amount of biogas used in the process is sufficient to provide the ethanol with a carbon intensity that does not exceed 10 $gCO_2e/MJ$.

In some embodiments, the biogas provides more than 50% of the methane (or NG) used for generating heat, power, or a combination thereof within the fuel production process. In some embodiments, the method comprises using at least 2000 MMBtu/day of manure derived biogas. In some embodiments, the carbon intensity of the biofuel or biofuel intermediate is reduced by at least 5 $gCO_2e/MJ$, at least 10 $gCO_2e/MJ$, at least 15 $gCO_2e/MJ$, or at least 20 $gCO_2e/MJ$ relative to if natural gas withdrawn from a commercial distribution system is used to generate heat and/or power for the production process instead of the biogas.

Of course, the above embodiments have been provided as examples only. It will be appreciated by those of ordinary skill in the art that various modifications, alternate configurations, and/or equivalents will be employed without departing from the scope of the invention. Accordingly, the scope of the invention is therefore intended to be limited solely by the scope of the appended claims.

The invention claimed is:

1. A process for producing biofuel comprising:
 (a) providing biogas from one or more biogas sources, said biogas comprising methane and provided in one or more mobile vessels, each mobile vessel pressurized to at least 2000 psig (13.79 MPa);
 (b) removing and depressurizing biogas from each of the one or more mobile vessels;

(c) generating heat, power, or a combination thereof, by combusting a gas comprising methane from the biogas removed and depressurized from the one or more mobile vessels; and (d) producing the biofuel or biofuel intermediate in a production process that includes treating a feedstock, said production process including the use of the heat, power, or a combination thereof, generated in step (c), wherein a quantity of biogas used to produce the heat, power, or combination thereof used in step (d) is sufficient to reduce a carbon intensity of the biofuel or biofuel intermediate by at least 5 gCO2e/MJ, and wherein a change in pressure provided by the depressurizing in step (b) is used to provide work for the production process, cooling for the production process, increased pressure for the production process, or a combination thereof.

2. The process according to claim 1, wherein the biofuel or biofuel intermediate produced in step (d) is ethanol, and wherein the production process comprises:

(i) treating the feedstock to produce one or more sugars;

(ii) adding a fermentation organism to a mixture comprising the one or more sugars and fermenting the one or more sugars to produce ethanol; and (iii) recovering the ethanol.

3. The process according to claim 2, wherein recovering the ethanol comprises a distillation.

4. The process according to claim 2, wherein said feedstock is corn grain, and wherein treating the feedstock to produce one or more sugars comprises milling the feedstock and adding amylase enzyme to the milled feedstock to hydrolyze starch therein.

5. The process according to claim 4, wherein the production process produces distiller's dried grain or distiller's dried grain with solubles.

6. The process according to claim 5, wherein the change in pressure produces cooled biogas, said cooled biogas used to cool distiller's dried grains or distiller's dried grain with solubles.

7. The process according to claim 2, wherein the feedstock comprises a lignocellulosic feedstock, and wherein treating the feedstock to produce one or more sugars comprises pretreating the feedstock at an elevated temperature to produce a pretreated slurry, and adding cellulase enzyme to the pretreated slurry to hydrolyze cellulose therein.

8. The process according to claim 1, wherein a change in pressure provided by the depressurizing in step (b) is used to provide cooling for the production process.

9. The process according to claim 8, wherein the change in pressure produces cooled biogas, said cooled biogas used to cool a circulating fluid directed to a condenser.

10. The process according to claim 1, wherein a change in pressure provided by the depressurizing in step (b) is used to provide work for the production process, wherein providing said work comprises passing the biogas removed from the one or more mobile vessels through a turboexpander.

11. The process according to claim 1, wherein the depressurizing in step (b) is conducted so as to provide the biogas at a pressure of at least 150 psig (1.03 MPa) for further processing.

12. The process according to claim 11, wherein the biogas at a pressure of at least 150 psig (1.03 MPa) is provided to a biogas upgrading unit comprising a membrane unit or a scrubbing unit without a substantial reduction in pressure, said membrane unit or scrubbing unit configured to remove carbon dioxide.

13. The process according to claim 1, wherein the biogas in the one or more mobile vessels is raw biogas or partially purified biogas, wherein the process includes upgrading the raw or partially purified biogas removed in step (b) prior to generating heat, power, or a combination thereof, in step (c), and wherein the process comprises collecting carbon dioxide produced from the upgrading and providing the collected carbon dioxide as part of a carbon capture, usage, and storage approach to reduce a carbon intensity of the biofuel.

14. The process according to claim 1, wherein the process is an integrated process that produces ethanol and renewable natural gas, and wherein there is heat exchanged between the ethanol production process and the renewable natural gas production process.

15. The process according to claim 1, wherein the biogas used in step (c) has a carbon intensity that does not exceed −100 gCO2e/MJ and is produced from manure.

16. The process according to claim 1, wherein the biogas provides more than 25% of the methane used for generating heat, power, or a combination thereof within the fuel production process.

17. The process according to claim 1, wherein the process comprises using at least 3000 MMBtu/day of manure derived biogas.

18. The process according to claim 1, wherein the biogas is derived from swine manure or dairy manure.

19. A process for producing one or more biofuels comprising:

(a) treating a feedstock to produce one or more sugars;

(b) adding a fermentation organism to a mixture comprising the one or more sugars and fermenting the one or more sugars to produce ethanol;

(c) recovering the ethanol;

(d) removing and depressurizing biogas from one or more mobile vessels pressurized to at least 2000 psig (13.79 MPa), said removed and depressurized biogas comprising methane;

(e) generating heat, power, or a combination thereof from at least a portion of the methane; and (f) using the heat, power, or combination thereof in step (a), step (b), step (c), or a combination thereof, thereby reducing a carbon intensity of the ethanol, wherein depressurizing the biogas in step (d) is conducted so as to provide work for step (a), step (b), step (c), or a combination thereof, cooling for step (a), step (b), step (c), or a combination thereof, or any combination thereof.

20. A process for producing one or more biofuels comprising:

(a) treating a feedstock to produce one or more sugars;

(b) adding a fermentation organism to a mixture comprising the one or more sugars and fermenting the one or more sugars to produce ethanol;

(c) recovering the ethanol;

(d) removing and depressurizing biogas from one or more mobile vessels having a pressure of at least 2000 psig (13.79 MPa), said removed and depressurized biogas comprising methane;

(e) generating heat, power, or a combination thereof from at least some of the methane; and (f) using the heat, power, or combination thereof in step (a), step (b), step (c), or a combination thereof, thereby reducing a carbon intensity of the ethanol, wherein said depressurizing comprises providing a pressure drop that cools the removed biogas, and wherein the process comprises providing heat transfer between the cooled biogas and a heat transfer medium and providing cooling for the process with the heat transfer medium.

\* \* \* \* \*